US005575993A

United States Patent [19]

Ward et al.

[11] Patent Number: 5,575,993
[45] Date of Patent: Nov. 19, 1996

[54] IONENE POLYMERS CONTAINING BIOLOGICALLY-ACTIVE ANIONS

[75] Inventors: James A. Ward, Eads; Fernando Del Corral, Memphis, both of Tenn.

[73] Assignee: Buckman Laboratories International, Inc., Memphis, Tenn.

[21] Appl. No.: 297,953

[22] Filed: Aug. 31, 1994

[51] Int. Cl.[6] ............................................. A01N 33/12
[52] U.S. Cl. .................. 424/78.1; 424/78.13; 424/78.14; 424/78.15; 424/78.3; 424/78.37; 424/78.38; 424/405; 514/252; 514/253; 514/357; 514/408; 514/422; 514/642; 514/643; 514/316; 514/332; 514/352; 514/396; 514/399; 514/400; 514/406; 514/428; 514/424; 514/425; 514/595; 514/597; 514/596; 514/598; 514/426; 514/588; 71/27; 71/30; 422/6; 422/7; 422/16; 422/154; 422/155; 422/156; 422/158; 422/159; 422/160; 43/132.1; 504/345; 252/405; 252/301.35; 510/234; 510/131; 510/383; 510/384; 510/382; 510/391; 510/475
[58] Field of Search .......................... 424/78.3, 78.37, 424/78.38, 78.1, 78.13, 78.15, 78.14, 329, 405; 514/252, 253, 316, 332, 357, 352, 396, 399, 400, 408, 406, 428, 424, 425, 422, 595, 596, 597, 598, 426, 642, 588, 643; 71/27, 30; 422/6, 154, 155, 156, 7, 158, 159, 160, 16; 43/132.1; 504/345; 252/515 R, 82, 84, 301.35, 405

[56] References Cited

U.S. PATENT DOCUMENTS

| 3,778,476 | 12/1973 | Rembaum et al. | 260/567.6 |
|---|---|---|---|
| 3,874,870 | 4/1975 | Green et al. | 424/78 |
| 3,898,336 | 8/1975 | Rembaum et al. | 424/25 |
| 3,931,319 | 1/1976 | Green et al. | 260/567.6 |
| 4,013,507 | 3/1977 | Rembaum | 195/1.8 |
| 4,027,020 | 5/1977 | Green et al. | 424/248.56 |
| 4,089,977 | 5/1978 | Green et al. | 424/329 |
| 4,111,679 | 9/1978 | Shair et al. | 71/67 |
| 4,506,081 | 3/1985 | Fenyes et al. | 548/523 |
| 4,581,058 | 4/1986 | Fenyes et al. | 71/67 |
| 4,778,813 | 10/1988 | Fenyes et al. | 514/357 |
| 4,851,532 | 7/1989 | Fenyes et al. | 544/357 |
| 4,960,590 | 10/1990 | Hollis et al. | 424/78 |
| 5,051,124 | 9/1991 | Pera | 71/67 |
| 5,093,078 | 3/1992 | Hollis et al. | 422/16 |

FOREIGN PATENT DOCUMENTS

| 0548796A1 | 6/1993 | European Pat. Off. . |
| 2160538 | 12/1985 | United Kingdom . |

Primary Examiner—Frederick Krass
Attorney, Agent, or Firm—Finnegan, Henderson, Farabow, Garrett & Dunner, L.L.P.

[57] ABSTRACT

Ionene polymers having biologically-active organic and/or inorganic anions are described. Methods to prepare the ionene polymers, compositions containing them and their methods of use are also described.

71 Claims, 2 Drawing Sheets

5,575,993

1

IONENE POLYMERS CONTAINING BIOLOGICALLY-ACTIVE ANIONS

FIELD OF THE INVENTION

This invention relates to new ionene polymers, methods for their preparation, and their various uses. More particularly, the new ionene polymers contain, as the cationic portion of the molecule, quaternary ammonium groups in the polymer backbone and, as part of the anionic portion of the molecule, at least one anion derived from a biologically-active compound. The new ionene polymers of the invention are water soluble and useful, for example, as herbicides, microbicides, plant growth regulators, pharmaceuticals, disinfectants, algicides, sanitizers, and preservatives.

BACKGROUND OF THE INVENTION

Ionene polymers or polymeric quaternary ammonium compounds (polyquats), i.e., cationic polymers containing quaternary nitrogens in the polymer backbone, belong to a well-known class of biologically-active compounds. See, e.g., A. Rembaum, *Biological Activity of Ionene Polymers*, Applied Polymer Symposium No. 22, 299–317 (1973). Ionene polymers have a variety of uses in aqueous systems such as microbicides, bactericides, algicides, sanitizers, and disinfectants. U.S. Pat. Nos. 3,778,476, 3,874,870, 3,898,336, 3,931,319, 4,013,507, 4,027,020, 4,089,977, 4,111,679, 4,506,081, 4,581,058, 4,778,813, 4,970,211, 5,051,124, and 5,093,078 give various examples of these polymers, their preparation, and their uses. U.S. Pat. Nos. 3,778,476, 3,898,536, and 4,960,590, in particular, describe insoluble trihalide containing ionene polymers. U.S. Pat. No. 4,013,507 describes ionene polymers which selectively inhibit the growth of malignant cells in vitro.

Cationic polymers in general, and quaternary ammonium ionene polymers in particular, have been shown to interact strongly with and attach themselves to surfaces, particularly polar surfaces. Most surfaces are, in general, anionic in nature. These electrostatic interactions are considered to be a basis for many uses of cationic polymers. For example, cationic polymers are very effective flocculating agents. The biocidal properties of ionene polymers are also believed to arise from, or to be enhanced by, electrostatic interactions between the cationic backbone of the ionene polymer and the surface of the biological substrate being treated by the ionene polymer.

A large number of relatively simple low molecular weight, monomeric organic and inorganic compounds are known and used for their biologically-active characteristics. The biologically-active compounds include, but are not limited to, pesticides, microbicides surfactants, sizing agents, plant growth regulators, fertilizers, disinfectants, fluorescence agents, preservatives and pharmaceuticals. Such compounds occur in all classes of compounds, e.g., as organic or inorganic acids, esters, amines, anhydrides or alcohols.

Though generally effective for their intended purpose, many biologically-active compounds suffer from one or more deficiencies which can prevent a particular compound from achieving its full activity. For example, in uses calling for application to a substrate, such as in the case of herbicides, the biologically-active compound may not always optimally adhere to the surface of the leaf or stem of the treated plant. The applied herbicide, therefore, may lose a measure of effectiveness due to run off during application. In other uses, the compound may be available only for immediate effect but no residual activity remains.

In accordance with this invention, the effectiveness of such biologically-active compounds can be improved by incorporating those compounds, as anions, into an ionene polymer. The anions are, therefore, integral components of the ionene polymer structure. Likewise, incorporating such biologically-active anions into the ionene polymer can also improve the ionene polymer's biological effectiveness.

SUMMARY OF THE INVENTION

This invention provides a water-soluble ionene polymer of formula I or II:

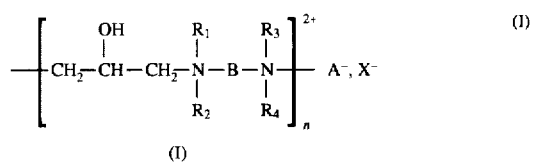

(I)

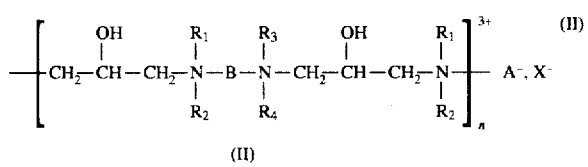

(II)

wherein n is an integer from 4 to 400 corresponding to the degree of polymerization of the polymer;

$R_1$, $R_2$, $R_3$ and $R_4$ represent the same or different substituent selected from the group consisting of hydrogen, a $C_1$ to $C_{16}$ alkyl group, a $C_1$ to $C_{16}$ alkyl group substituted with one or more hydroxyl groups, a benzyl group and a benzyl group substituted with one or more $C_1$ to $C_{16}$ alkyl groups;

B represents a divalent $C_2$ to $C_{16}$ aliphatic hydrocarbon radical which can be substituted by hydroxyl, a divalent $C_5$ to $C_9$ cyclic hydrocarbon radical, a di-($C_2$ to $C_6$)-alkylene ether, a phenylene or alkyl-substituted phenylene radical, or the divalent group $R_1R_2NBNR_3R4$ of formula I or II represents a divalent radical of the structure:

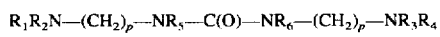

$$R_1R_2N-(CH_2)_p-NR_5-C(O)-NR_6-(CH_2)_p-NR_3R_4$$

where p is an integer from 2 to 6, $R_1$, $R_2$, $R_3$ and $R_4$ are as defined above, and $R_5$ and $R_6$ are the same or different and are selected from the group consisting of hydrogen and a $C_1$ to $C_{16}$ alkyl group, or the divalent radical $R_1R_2NBNR_3R_4$ forms a heterocyclic group selected from 1,2-pyrazolidinyl, 1,3-imidazolindiyl, 1,4-piperazindiyl, aminopyrrolidinyl, and aminopiperidiyl wherein the heterocyclic group may be substituted with one or more groups selected from a $C_1$ to $C_6$ alkyl group, a hydroxyl group, a halide, and a phenyl group.

$A^-$ is an anion derived from a biologically-active compound having at least one acid functionality; and $X^-$ is an anion derived from a mineral or organic acid.

In the ionene polymers of the invention, the degree of substitution (D.S.) defines the amount of the active anion "$A^-$" present. For ionene polymers of formula I, the degree of substitution of the polymer may vary from about 0.005 to 0.5 (one half). Ionene polymers of formula II can have a D.S. which may vary from about 0.005 to 0.33 (one third).

This invention also provides a method to prepare the novel ionene polymers using partially or fully protonated ammonium monomers containing a biologically-active anion. Polymerizing such monomers yields an ionene polymer having the biologically-active anion as an integral part of the ionene polymer.

The biological activity of the ionene polymers of formula I and II results from the ionene polymer backbone and/or the biologically-active anion. The ionene polymers may not only possess the activity and uses known for ionene polymers, but also the activity and uses of the biologically-active anion. To some extent, then, only the availability of biologically-active anions limits the preparation, activity and use of ionene polymers according to this invention. This invention, therefore, also provides various compositions and methods of use for the novel ionene polymers.

The detailed description which follows sets out additional features and advantages of the invention. The additional features and advantages will, at least in part, be apparent from the description or may be learned by the practice of the invention. The objectives and other advantages of the invention will be realized and attained by the invention as described, claimed, and shown in the accompanying figures.

DETAILED DESCRIPTION OF THE INVENTION

Figure 1:
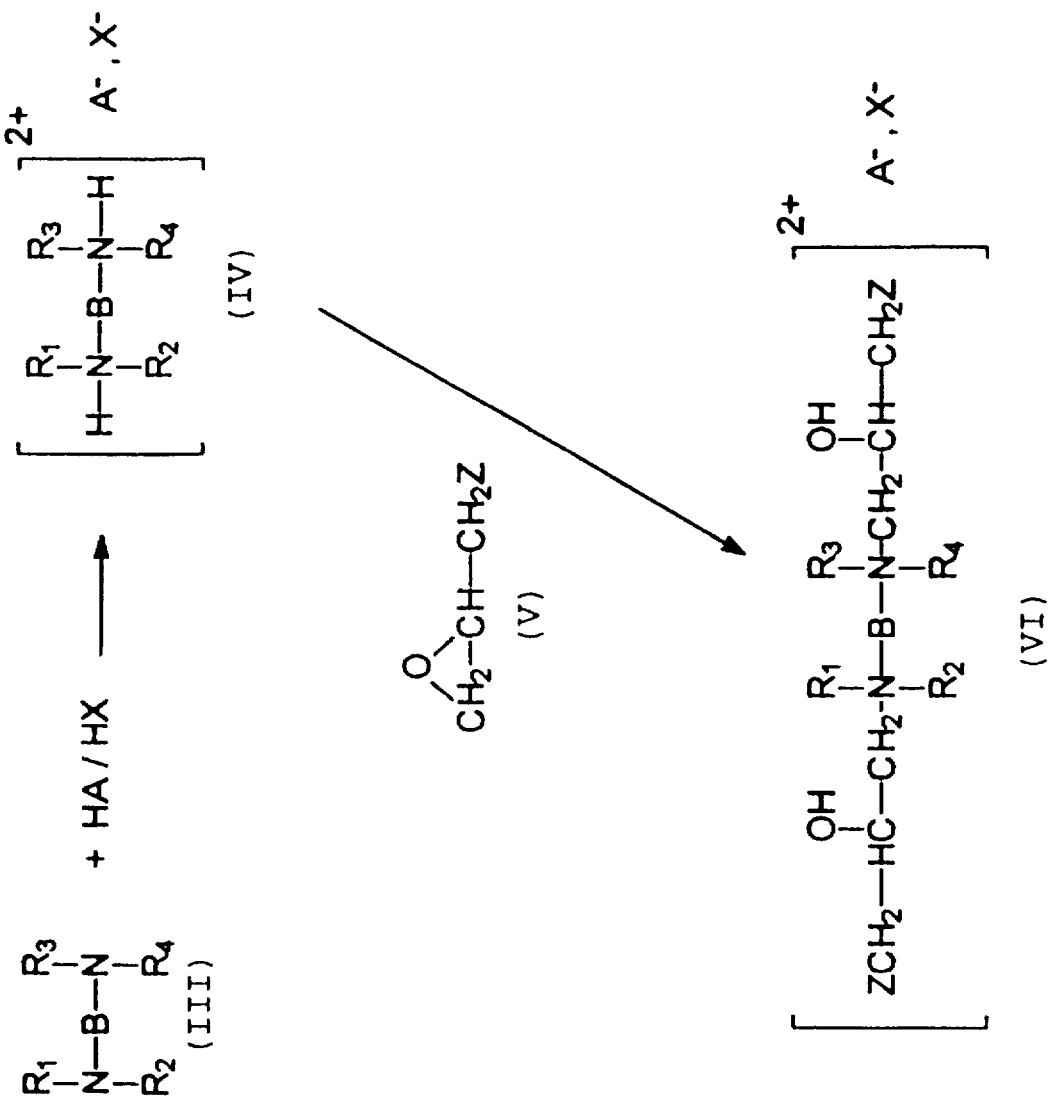
FIGS. 1 and 2 depict reaction schemes to prepare the ionene polymers of this invention.

In a first embodiment, this invention provides novel, water-soluble ionene polymers of formula I or II:

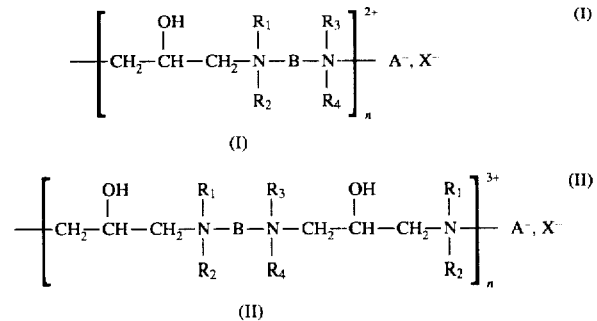

In each of the above formulas, the variables and substituents have the following definitions.

The variable "n" is an integer from about 4 to 400 corresponding to the degree of polymerization of the polymer. Preferably, "n" ranges from about 5 to 100 and most preferably, from about 5 to 50. Generally speaking, ionene polymers having this degree of polymerization can have molecular weights ranging from about 1,000 to 20,0000. Preferably, the ionene polymers of this invention have molecular weights ranging from about 1,000 to 10,000 and most preferably about 3,000 to 5,000.

The substituents $R_1$, $R_2$, $R_3$ and $R_4$ represent the same or different groups selected from hydrogen; $C_1$ to $C_{16}$ alkyl groups; $C_1$ to $C_{16}$ alkyl groups substituted with one or more hydroxyl groups; a benzyl group; or a benzyl group substituted with one or more $C_1$ to $C_{16}$ alkyl groups. Preferably, $R_1$, $R_2$, $R_3$ and $R_4$ are methyl, ethyl or benzyl and most preferably methyl. As used herein, an alkyl group may be a straight chain or a branched chain.

"B" represents a divalent $C_2$ to $C_{16}$ aliphatic hydrocarbon radical which can be substituted with hydroxyl, a divalent $C_5$ to $C_9$ cyclic hydrocarbon radical, a di-($C_2$ to $C_6$)-alkylene ether, a phenylene or alkyl-substituted phenylene radical. Preferably, B is methylene, ethylene, propylene, 2-hydroxy propylene, butylene isobutylene, hexylene, diethylene ether, or phenylene.

Alternatively, the divalent group $R_1R_2NBNR_3R_4$ of formula I or II represents a divalent radical derived from the reaction product of urea and an aliphatic mixed tertiary/primary amine. In this alternative, the divalent group $R_1R_2NBNR_3R_4$ has the structure:

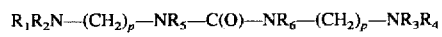

$$R_1R_2N-(CH_2)_p-NR_5-C(O)-NR_6-(CH_2)_p-NR_3R_4$$

The variable "p" is an integer from 2 to 6, preferably 2 to 4, and most preferably 2 or 3. $R_5$ and $R_6$ are the same or different and are selected from the group consisting of hydrogen and a $C_1$ to $C_{16}$ alkyl group. Hydrogen, methyl and ethyl are preferred for substituents $R_5$ and $R_6$. U.S. Pat. No. 4,506,801, which is incorporated herein by reference, describes ionene polymers derived from urea diamines.

The divalent radical $R_1R_2NBNR_3R_4$ may also form a heterocyclic group selected from 1,2-pyrazolidinyl, 1,3-imidazolindiyl, 1,4-piperazindiyl, aminopyrrolidinyl, and aminopiperidiyl. These heterocyclic groups may be substituted, for example, with one or more groups selected from a $C_1$ to $C_6$ alkyl group, a hydroxyl group, a halide, and a phenyl group.

"$A^-$" is an anion derived from a biologically-active, organic or inorganic, compound having at least one acid functionality. The biologically-active anion "$A^-$" may be a monovalent, divalent, trivalent, tetravalent, or otherwise polyvalent anion. Thus, "$A^-$" symbolizes an anion generally and is not limited to monovalent anions. The charge of a particular anion "$A^-$" depends on its corresponding biologically-active compound.

The biologically-active anion "$A^-$" can be provided by virtually any biologically-active compound having acid functionality capable of reacting with an amine to form a protonated amine salt. This includes organic and inorganic biologically-active compounds. Preferably, the biologically-active compound yielding the anion "$A^-$" is, therefore, a Brönsted acid.

The biologically-active acid compounds include, but are not limited to, pesticides, surfactants, sizing agents, plant growth regulators, fertilizers, disinfectants, preservatives, microbicides, dispersants, and therapeutic agents, such as pharmaceuticals or topical antiseptics. Chemicals known broadly as pesticides have achieved widespread use throughout the world for many agronomic and horticultural applications. Pesticides include, but are not limited to, herbicides, fungicides, insecticides, sporacides, and nematicides. Pesticides may also include chemicals used for other types of applications such as fertilizers, plant growth regulators, disinfectants, defoliants, and seed protectants. Fertilizers are chemicals which may be applied to foliage, although fertilizers are not considered to be pesticides.

Sources for the selection of compounds having the requisite acid functionality include, for example, such publications as The Farm Chemicals Handbook, The Physician's Desk Reference or Drugs of the Future, all incorporated herein by reference. Tables 1 and 2 below provide examples of some biologically-active organic and inorganic anions "$A^-$" and their uses.

TABLE 1

Examples of Organic Biologically-Active Compounds

| Activity | Common Name | Chemical Name |
|---|---|---|
| Pesticide | Citronellic Acid | 3,7-dimethyl-6-octanoic acid |
| Herbicide | 2,4D | 2,4-dichlorophenoxyacetic acid |
| | endothall | 7-oxabicyclo[2,2,1]haptene-2-3-dicarboxylic acid |
| | chloramben | 3-amino-2,5-dichlorobenzoic acid |
| | glyphosate | N-(phosphono-methyl) glycine |
| Microbicide | BHAP | Bromohydroxyacetophenone |
| | orthophenylphenol | 2-hydroxybiphenyl |
| | Guanidine acetic acid | Guanidine acetic acid |
| | 3-Indole propionic acid | Indole-3-propionic acid |
| Plant growth Regulator | Gibberellic acid | 2,4a,7-Trihydroxy-1-methyl-8-methylenegibb-3-ene-1,10-dicarb-oxalic acid 1,4a-lactone |
| | endothall | 7-oxabicyclo[2,2,1]haptene-2-3-dicarboxylic acid |
| | ethephon | (2-chloroethyl)phosphoric acid |
| | IBA | Indole-3-butyric acid |
| | NAA | 1-Naphthaleneacetic acid |
| Fluorescence | fluorescein | 3',6'-dihydroxyspiro[isobenzofuran-1(3H),9'-[9H]xanthen]-3-one |
| Scale Control | Citric acid | 2-Hydroxy-1,2,3-propanetricarboxylic acid |
| Pharmaceutical | Amethopterin (cancer treatment) | N-[4-[[(2,4-Diamino-6-pteridinyl)-methyl]methyl-amino]benzoyl]-1-glutmic acid |
| | PABA (sunscreen) | p-Aminobenzoic acid |
| | aspirin | acetyl salicylic acid |
| | p-HBA | para-hydroxybenzoic acid |
| Disinfectant | Phenol | Phenol |
| Sizing Agent | Abietic, acid | 1,2,3,4,4a,4b,5,6,10,10a-Decahydro-1,4a-dimethyl-7-(1-methylethyl)-1-phenanthrenecarboxylic acid |
| Surfactant | Stearic Acid | Octadecanoic acid |
| | Lauric Acid | Dodecanoic acid |
| | Capric Acid | Decanoic acid |

TABLE 2

Examples of Inorganic Biologically-Active Compounds

| Activity | Common Name | Chemical Name |
|---|---|---|
| Microbicides | tri-halides | $Br_3^-$, $I_3^-$, $BrI_2^-$, $ClI_2^-$, $ClBr_2^-$, $Br_2I^-$, $I_2Cl^-$, etc. |
| | oxyhalides | $OCl^-$, $OBr^-$, $OI^-$ |
| Termiticides/ | borates | $HBO_3^-$ |
| Wood Preservatives | tetraborates | $B_4O_7^{2-}$ |
| Sanitizers | poly-halides | $I_3^-$, $I_5^-$, $I_7^-$, etc. |

In addition to the activity shown in Table 2, inorganic biologically-active anions, such as trihalide and oxyhalide anions, are also known as disinfectants. Preferred trihalide anions include, for example, $Br_3^-$, $I_3^-$, $BrI_2^-$, $ClI_2^-$, $ClBr_2^-$, $I_2Cl^-$ and $Br_2I^-$, with $I_3^-$ being particularly preferred. Preferred oxyhalide anions include $OCl^-$, $OBr^-$, and $OI^-$.

The anion "$X^-$" is derived from a mineral (e.g., inorganic) or an organic acid, HX. As with "$A^-$", the anion "$X^-$" can be a monovalent, divalent, trivalent, tetravalent, or otherwise polyvalent anion of a mineral acid. "$X^-$" symbolizes the anion generally and is not limited to monovalent anions. Similarly, HX is not limited to monoprotic acids. Mineral acids include, for example, hydrofluoric acid, hydrochloric acid, hydrobromic acid sulfuric acid, nitric acid, and phosphoric acid. Organic acids include, but are not limited to, formic acid, acetic acid, propionic acid, butyric acid, valeric acid, caproic acid, cyclohexanecarboxylic acid and benzoic acid. Acetic acid is preferred. Preferred, anions include halide anions and particularly $Cl^-$.

In general, the water-soluble, biologically-active ionene polymers of the invention cannot be prepared by any simple process such as mixing an anion of a biologically-active compound with an existing ionene polymer which has been formed by known processes. Sufficient ion exchange does not occur in ionene polymers by such a simple equilibrium-shifting process. For example, an ionene polymer made by the reaction of a di-tertiary amine, hydrochloric acid, and epichlorohydrin has chloride anions. In order for the chloride anions of that ionene polymer to be replaced by a biologically-active anion using an equilibrium-shifting process, a large excess of the biologically-active anion would be required and only a small fraction would replace the chloride ions.

A second embodiment of this invention, therefore, relates to the preparation of ionene polymers containing biologically-active anions where those anions are intimately associated with and distributed throughout the ionene polymer. Ionene polymers of formulas I or II can be conveniently prepared by a general method shown in FIGS. 1 and 2. The general method proceeds by the following steps:

1) complete or partial neutralization of a diamine with a biologically-active acidic compound to form a protonated diamine salt;

2) formation of an intermediate by reacting the protonated diamine salt with an epihalohydrin; and 3) polymerizing the intermediate with additional diamine or other amine to form an ionene polymer according to this invention.

The general method may be, and preferably is, carried out in a single reaction vessel or zone using an aqueous medium.

Figure 2:
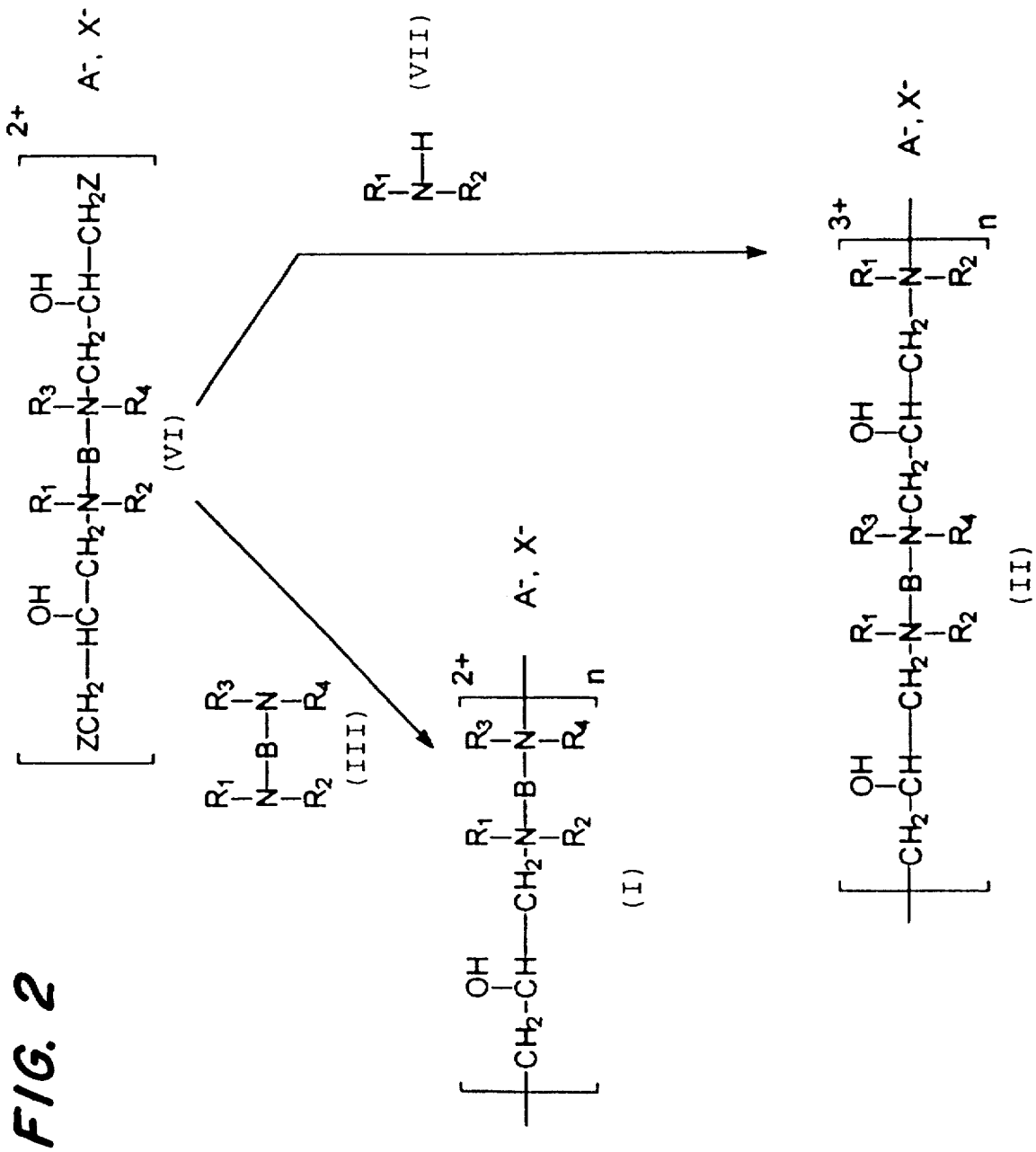

In this general method, all of the quaternary ammonium (nitrogen containing) groups in the ionene polymer result from the reaction of the tertiary, secondary, or even primary amines. The associated anion (the gegenion) comes from two sources. In the first part of the process, a biologically-active or other acid reacts with a portion of the amine groups present to protonate all or a portion of those amine groups. All of the anions from this initial neutralization or protonation step end up as anions on the finished ionene polymer. The other anions come from the halide of the epihalohydrin employed in the polymerization step. Referring to FIGS. 1 and 2, a detailed description of this method follows:

As shown in FIG. 1, a diamine compound, III, is neutralized with a biologically-active, acidic compound, HA, alone or in combination with another acid, HX. At least a portion of the amine groups reacts with the acidic groups of the compound HA to partially or fully protonate the amine groups and form the salt IV. The neutralization reaction can be accomplished by any means known in the art but preferably occurs by adding the compound HA to an aqueous solution of the bis-tertiary diamine.

Any diamine of the formula III may be neutralized by the biologically-active acidic compound HA. Because the diamine III is a starting material for the ionene polymers of the invention, the substituents $R_1$, $R_2$, $R_3$ and $R_4$ are the same as those defined above for the ionene polymers of formula I and II, including the preferred embodiments. Each substituent may be the same or different from the others. Particularly preferred diamines of formula III include, for example:

N,N,N',N'-tetramethylethylenediamine (TMEDA),

N,N,N',N'-tetramethyl-1,3-propylenediamine,

N,N,N',N'-tetramethyl-1,3-butylenediamine,

N,N,N',N'-tetramethyl-1,4-butylenediamine,

N,N,N',N'-tetramethyl-1,6-hexylenediamine, bis(beta-dimethylaminoethyl)ether, and 1,3-bis(dimethylamino)-2-propanol.

Alternatively, the diamine of formula III can be a polyamine derived from the reaction product of urea and an aliphatic mixed tertiary/primary amine, a ureadiamine. In this alternative, the ureadiamine has the structure:

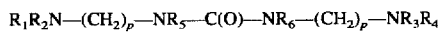

The variable "p" is an integer from 2 to 6, preferably 2 to 4, and most preferably 3. $R_5$ and $R_6$ may be the same or different and are selected from hydrogen and a $C_1$ to $C_{16}$ alkyl group. Hydrogen, methyl and ethyl are preferred for substituents $R_5$ and $R_6$. U.S. Pat. No. 4,581,058 describes ionene polymers derived from urea diamines and is incorporated herein by reference. A preferred ureadiamine has the following formula:

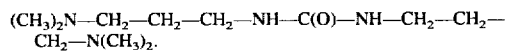

A preferred urea diamine can be conveniently prepared by heating urea and dimethylaminoethylamine or dimethylaminopropylamine with ammonia evolved as a by-product. When conversion to the urea diamine approaches 100%, ammonia evolution ceases indicating the reaction is complete. Other preferred urea diamines are those obtained by the reaction of dialkylalkylene diamines where the alkyl group is a $C_1$ to $C_{16}$ alkyl, preferably methyl, ethyl, or propyl and the alkylene group is a $C_2$ to $C_6$ alkylene group, preferably $C_2$ to $C_4$.

When the divalent radical $R_1R_2NBNR_3R_4$ is a heterocyclic group, the diamine compound III may be selected from 1,2-pyrazolidine, 1,3-imidazolidine, 1,4-piperazine, aminopyrrolidine, and aminopiperidine. As discussed above, these heterocyclic diamines may be substituted with, for example, one or more groups selected from a $C_1$ to $C_8$ alkyl group, a hydroxyl group, a halide, and a phenyl group.

The neutralization reaction between the diamine III and the compound HA can be controlled to form a partially or fully protonated diamine compound of formula IV. In compound IV, the protonated amine cation is ionically bound to the anionic portion of the biologically-active compound, "A⁻."

The stoichiometric ratio of moles of compound HA to moles of diamine can vary with the number of moles of compound HA and/or the number of acidic groups in compound HA used to neutralize the diamine III. For example, when reacting a compound HA having only one acidic group, two moles of HA can be added to completely neutralize each mole of diamine. Alternatively, to fully react a mole of diamine with a biologically-active diacid, only one mole of the diacid is required. The stoichiometric ratio may also vary in those biologically-active compounds HA having more than one acidic group where not all of the acidic groups are permitted or available for reaction with the diamine. Thus, the diamine of formula III may be neutralized with up to one equivalent of a biologically-active acid, HA, per amine group.

The stoichiometric ratio between the compound HA and a diamine generally determines the amount of biologically-active anions, "A⁻", present in the final ionene polymer. If a biologically-active acid is the only acid used in the neutralization reaction, then all of the anions associated with the protonated diamine IV will come from the biologically-active acid.

The ionene polymers according to the invention, however, do not require all anions to be derived from biologically-active acidic compounds. In fact, in a preferred embodiment, the ionene polymer may have less than a complete stoichiometric number of biologically-active anions per quaternary ammonium unit. Ionene polymers having less than the stoichiometric number of biologically-active anions are conveniently prepared by neutralizing a diamine compound III with less than the stoichiometric amount of biologically-active acidic compound, HA.

In neutralization reactions not employing stoichiometric amounts of biologically-active compound HA to diamine III, a subsequent acid may be employed to completely neutralize the diamine. The amount of subsequent acid employed raises the total molar amount of acid employed to approximately equal to, or equal to, the stoichiometric amount of amine groups present. The subsequent acid may be a different biologically-active compound HA or a mineral or organic acid, HX. This is shown in FIG. 1 as the reactant HA/HX. The complete neutralization reaction employing the reactant HA/HX can occur simultaneously or sequentially in any order.

When using one or more different biologically-active compounds, each compound may be known for the same or different activity as the other biologically-active compound. The subsequent biologically-active compound may be used to fully or partially neutralize the remaining amine groups in the diamine. If another biologically-active compound HA is used in an amount to also only partially neutralize the remaining amine groups, a mineral acid or another biologically-active compound can be employed to fully neutralize the diamine. Thus, multiple combinations of biologically-active anions can be prepared for a given ionene polymer according to the invention.

The "less-than-stoichiometric" ionene polymers according to this invention contain at least sufficient biologically-active anions to possess the desired function and/or level of activity. For example, a herbicidal ionene polymer according to this embodiment of the invention contains sufficient herbicidally-active anions to give the ionene polymer its herbicidal properties. Degrees of herbicidal activity such as quick kill or duration of efficacy may be achieved by employing more or less herbicidal anions per ionene polymer, i.e., raising or lowering the degree of substitution.

As discussed above, any mineral or organic acid, HX, can be used as the subsequent acid when reacting less than the stoichiometric amount of biologically-active compound HA. Thus, there can be used halogen acids such as hydrochloric, hydrobromic or hydroiodic acid; acids of phosphorus such as phosphoric or phosphorous acids; acids of sulphur such as sulfuric or sulphurous acids or an organic acid such as acetic acid.

Use of a subsequent acid yields a protonated diamine compound IV with mixed anions and permits variation in the degree of substitution, D.S. With or without adding a subsequent acid, the reaction between the acid and the diamine yields a protonated diamine compound IV starting material for the formation of an ionene polymer according to the invention.

The neutralization reaction can be readily accomplished by techniques known to the art. Preferably, the neutralization occurs in an aqueous medium, and most preferably in water. Generally, this neutralization, a simple acid/base reaction, proceeds essentially spontaneously at room temperature. In some instances, cooling may actually be required.

As shown as a second step in FIG. 1, the protonated diamine IV reacts with an epihalohydrin V to forman intermediate compound VI having quaternary ammonium groups and halogen-containing end groups capable of further reaction, e.g., polymerization. The acid anions "A$^-$" and/or "X$^-$" remain intimately associated with the quaternary ammonium groups of the intermediate compound via ionic bonds.

Almost any epihalohydrin V, substituted or unsubstituted, can be used to form the intermediate compound VI. Preferred epihalohydrins include epichlorohydrin, epibromohydrin, epifluorohydrin and epiiodohydrin. Thus, the group "Z" in compounds V and VI represents F, Cl, Br or I. Epichlorohydrin is particularly preferred.

The protonated diamine IV and the epihalohydrin V react under relatively mild conditions by means known in the art. The protonated diamine reacts by opening the epoxide rings of the epihalohydrin forming an electrophilic radical which adds to one of the tertiary amine groups forming a halogenated intermediate compound of formula VI. The reaction can readily be accomplished in aqueous medium or suitable organic solvents (e.g., lower alkyl alcohols) and, if necessary, upon application of moderate heating, for example, from about 30° to 60° C. Preferably, the reaction takes place in water or an aqueous medium and, most preferably, in the water-based reaction medium used to prepare the protonated diamine compound IV. Most preferably, the first two steps, indeed all steps, in the preparation of ionene polymers according to this invention occur in the same reaction vessel or zone.

As discussed above, the biologically-active anion "A$^-$" can be provided by any biologically-active compound HA having acid functionality capable of reacting with the diamine III to form a protonated diamine compound IV. Since the polymer forming reaction generally occurs in basic medium, the biologically-active acid compound should be at least reasonably stable in a basic environment. In addition, it should preferably be relatively inactive toward epoxide groups while free epihalohydrin is present in the reaction mixture. Likewise, the organic compound containing acid functionality should not readily esterify the free hydroxyl generated by the reaction between the epoxide group of the epihalohydrin and the protonated amine salt.

As shown in FIG. 2, the intermediate compound VI can then be polymerized with additional diamine III or an amine VII under conditions sufficient to form the ionene polymers according to this invention. The reaction on the left side of FIG. 2 depicts the polymerization of intermediate compound VI with a diamine III to form an ionene polymer of formula I. The reaction on the right side of FIG. 2 shows the polymerization of intermediate compound VI with a secondary amine of formula VII which yields the ionene polymer of formula II.

The diamine III used to polymerize the intermediate compound VI can be the same or different as used to prepare the protonated diamine compound VI. Any amine of formula VII can be used in the polymerization reaction. Preferred amines include, for example, dimethylamine, diethylamine, dipropylamine, methylethylamine. Dimethylamine is most preferred.

Either polymerization can be carried out by means known in the art. The intermediate compound VI readily polymerizes with the diamine III or the secondary amine VII requiring no additional reactants or catalysts. The polymerization reaction takes place readily upon application of moderate heat, e.g., from about 75° to 105° C., preferably approximately 80° to 95° C. In a preferred embodiment, the diamine III or the secondary amine VII is added to a warm solution, for example, approximately 40° to 65° C., then subsequently heated to effect polymerization or complete the reaction.

In its course, the polymerization displaces the terminal halogen "Z" as a halide anion "Z$^-$" and forms new quaternary ammonium groups. The halide anion "Z$^-$" remains associated with the growing ionene polymer ionically bound to the newly formed quaternary ammonium group. In the definition of the final ionene polymer products I and II shown in FIG. 2, the anion "X$^-$" is the same as and includes the halide ion "Z$^-$". Thus, in a preferred embodiment, the anion "X$^-$" in the protonated diamine compound IV is the same as the halogen in the epihalohydrin used to form the intermediate compound VI. For example, the anion "X$^-$" may be Cl$^-$ derived from hydrochloric acid used as HX and epichlorohydrin used as the epihalohydrin.

When employing a urea diamine as the diamine III to effect the polymerization, one convenient method to control the molecular weight of the final polymer results from varying the reaction time of the reaction used to prepare the urea diamine. If one stops the urea diamine preparation reaction before achieving 100% conversion, then any final ionene polymer made from that urea diamine preparation will have a lower molecular weight than an ionene polymer prepared from a fully converted urea diamine preparation. One can obtain the same result by using less then the stoichiometric ratio of reactants to prepare the urea diamine and using that preparation in the polymerization reaction.

Additionally, when epibromohydrin, hydrogen bromide, and bromine are used in the process, the resulting ionene polymer may contain up to 100% tri-bromide. It may even be possible to conduct the polymerization reaction in such a manner so that two or more tri-halides are on the same ionene polymer molecule. As follows from the above discussion, one of ordinary skill would appreciate that other variations include mixed tri-halides, e.g., I$_2$Cl$^-$.

The ionene polymers of the formulas I and II, may also be capped, i.e., have a specific end group. Capping may be achieved by means known in the art. For example, an excess of either reactant used to make the ionene polymer can be employed to provide a capping group. Alternatively, a calculated quantity of a monofunctional tertiary amine or monofunctional substituted or unsubstituted alkyl halide can be reacted with an ionene polymer to obtain a capped ionene polymer. Ionene polymers can be capped at one or both ends. U.S. Pat. Nos. 3,931,319 and 5,093,078 describe capped ionene polymers and their microbicidal properties. The disclosures of which are incorporated herein by reference.

The ionene polymers of formulas I and II may also be cross-linked with primary, secondary or other polyfunctional amines using means known in the art. The ionene polymers can be cross-linked either through the quaternary nitrogen atom or through another functional group attached to the polymer backbone or to a side chain.

U.S. Pat. No. 3,738,945 and Reissue U.S. Pat. No. 28,808 disclose cross-linked ionene polymers prepared using various cross-linking coreactants. The disclosures of which are incorporated herein by reference. The Reissue Patent describes the cross-linking of ionene polymers prepared by the reaction of dimethylamine and epichlorohydrin. The cross-linking coreactants listed are ammonia, primary amines, alkylenediamines, polyglycolamines, piperazines, heteroaromatic diamines and aromatic diamines.

U.S. Pat. No. 5,051,124, the disclosure of which is incorporated herein by reference, describes cross-linked ionene polymers resulting from the reaction of dimethylamine, a polyfunctional amine, and epichlorohydrin. The patent also describes methods of inhibiting the growth of microorganisms using such cross-linked ionene polymers.

Other examples of various cross-linked ionene polymers and their preparation are provided in U.S. Pat. Nos. 3,894,946, 3,894,947, 3,930,877, 4,104,161, 4,164,521, 4,147,627, 4,166,041, 4,606,773, and 4,769,155. The disclosures of each of these patents are incorporated herein by reference.

The amount of biologically-active anions, "$A^-$", present in a given ionene polymer according to the invention is defined by the "degree of substitution" (D.S.) of that polymer. The term "degree of substitution" refers by analogy to known ionene polymers which typically contain only halide anions, such as $Cl^-$. Because one could view the biologically-active anions as replacing or substituting for the typical halide anions of an ionene polymer, the "degree of substitution" for a given ionene polymer of this invention refers to the number of anions which are biologically-active anions, "$A^-$." Thus, a D.S. of 0.5 means that 50% of the anions are biologically-active anions, "$A^-$". The amount of biologically-active compound HA reacted with a diamine can be selected according to the degree of substitution desired in the product ionene polymer.

One of ordinary skill would understand that D.S. will also depend on the valency of the biologically-active anions "$A^-$". Therefore, when using divalent or otherwise polyvalent biologically-active anions, the D.S. may refer to the number of anionic charges substituted rather than the number of actual anions replaced.

The degree of substitution, therefore, defines the number of biologically-active anions "$A^-$" ionically bound to the ionene polymer. When the protonated diamine IV contains one biologically-active anion "$A^-$" per amine group, a maximum D.S. will be achieved in the product ionene polymer. In general, the ionene polymers of formula I have a D.S. less than or equal to 0.5 (one-half), preferably 0.005 to 0.5. Similarly, the ionene polymers of formula II have a D.S. less than or equal to 0.33 (one-third), preferably 0.005 to 0.33. That is, because protonated diamine reacts with the epihalohydrin, a portion of the anions bound to the polymer will be halide anions from the epihalohydrin. The other anions come from the biologically-active compound HA used to neutralize the diamine III and produce a protonated diamine IV.

For various reasons it may not be desirable or possible to attain degrees of substitution less than or equal to 0.5 for ionene polymers of Formula I or less then and equal to 0.33 for those of Formula II. It is recognized, therefore, that the minimum degree of substitution has to correspond to at least one active anion per ionene polymer molecule.

Since the degree of polymerization (n) in the formulae varies over a wide range, then D.S. must also vary, as D.S. is inherently dependent on the degree of polymerization. The preferred range of D.S. may, therefore for Formula I, vary from about 0.005 to 0.5, although there might be very large polymers which have a large n. In that case D.S. might be smaller than 0.005. Similarly, for ionene polymers of Formula II, preferably D.S. may vary from about 0.005 to 0.33, but with very large polymers D.S. may be less than 0.005.

One significant advantage gained by incorporating the biologically-active compounds into an ionene polymer in the manner of this invention is a substantial increase in water solubility as compared to that of the most biologically-active compounds themselves. For example, the water solubility of the herbicide 2,4-D is highly dependent on pH. When incorporated into an ionene polymer according to this invention, the 2,4-D ionene polymer product is nearly or even completely water soluble without regard for pH. Also, for example, an ionene polymer according to the invention having a tri-iodide as the anionic portion of the polymer is water soluble. Thus, much higher concentrations of the effective compound, that is, the biologically-active anion, can be achieved.

For the purpose of this invention, an ionene polymer is defined as water-soluble if solutions containing at least about 1000 ppm in water at 25° C. of the ionene polymer can be prepared. More preferably, the water solubility is at least about 5000 ppm. An important distinction must be made between this definition of water-soluble and what is meant by an effective amount of an ionene polymer for a given use. Often the effective amount of an ionene polymer according to the invention can be less than 1000 ppm. More importantly, the effective amount also depends on the D.S. of the ionene polymer, i.e., the amount of biologically-active anions present. The water solubility, however, refers to the solubility of the entire biologically-active ionene polymer itself. Thus, while the ionene polymers of this invention meet the definition of water-soluble, a solution containing an effective amount of the ionene polymer may not necessarily be that concentrated.

If a high degree of water solubility is not desirable for a specific application, adjustments to the polymer can be made to affect its hydrophilicity and hydrophobicity and control solubility. These adjustments are well-known in the art. One means of control, for example, is to select hydrophobic anions and/or increase the amount of such anions in the polymer. End capping reactions, discussed above, can also be carried out to place hydrophobic groups on the ends of the polymer chains. A number of useful end-capping techniques are taught by U.S. Pat. Nos. 3,931,319 and 5,093,078. Also, the use of ditertiary amines having long chain hydrocarbon sequences as the starting material will tend to reduce water solubility.

As discussed above, the utility of the ionene polymers of this invention may be defined by the biologically-active anion "$A^-$", the ionene polymer and/or both. As such, an ionene polymer according to this invention may be used in any manner appropriate for that utility.

For example, if the ionene polymer is a herbicide, the ionene polymer may be the active ingredient in a herbicide composition or formulation which would be a dust or powder or a solution, emulsion or suspension. Whatever its usable form, the ionene polymer may be used with other adjuvants such as carriers, stabilizers, emulsifiers, or surfactant.

Thus, a person applying a herbicide, for example, usually acquires the product as a formulation which contains not only the active ingredient but also other materials. The product (formulation) is typically a liquid or a powder which is designed to be mixed with water so that the active ingredient will remain dissolved or suspended uniformly throughout the water during application. Herbicide formulations may contain other agents (adjuvants) which improve the water/herbicide suspension and facilitate the coverage of the application over the target plants. An adjuvant is an ingredient added to a formulation, e,.g., a herbicide or other agrochemical formulation, to change or assist the activity of the principal active ingredient. An adjuvant may be an oil, surface tension reducing agent, solvent, activator, stabilizer, sticker, and a foaming or anti-foaming agent. The choice of adjuvant depends on the physical or chemical property to be modified. Chemically, surfactants are the most important and widely used adjuvants. Surfactants may affect many properties of the formulation such as a solubility, volatility, specific gravity, corrosiveness, efficacy, and freezing and flash points.

The performance (or effectiveness) of a herbicide in any application is dependent on the quantity applied, the method of application, and the environmental conditions during the application. Generally, the grower or person applying a herbicide wants to achieve a desired result with the least amount of chemical and at the lowest cost. The ionene polymers of this invention having anions derived from a herbicide, therefore, may be used as active ingredients in new herbicidal compositions which meet or exceed the biological objective of the herbicide while using less of the herbicide itself. Thus, the ionene polymers according to the invention improved performance while reducing cost and chemical usage. The invention, therefore, provides both economic and environmental advantages.

Accordingly, when the ionene polymer of the invention is a herbicide, the invention relates to herbicidal compositions comprising an effective amount of that ionene polymer. Methods of using that ionene polymer as a herbicide are also contemplated, where the ionene polymer, either alone or in a herbicidal composition, is applied to vegetation in a herbicidally-effective amount.

As another example, if the ionene polymer is a pharmaceutical, it may be employed with pharmaceutically acceptable carriers, in solution, as a powder, or in a tablet or other pill. Depending upon its use, the ionene polymer can be administered using any pharmaceutically acceptable form or technique. If the ionene polymer is a pharmaceutical, the invention also relates to pharmaceutical compositions comprising an effective amount of the ionene polymer and methods of treatment administering to a host in need thereof an effective amount of the ionene polymer. The term "host" includes, but is limited to, animals, livestock, pets, plants or humans.

When an ionene polymer according to the invention contains a sanitizer or disinfectant such as triiodide, $I_3^-$, as the biologically-active anion, that ionene polymer can then be used in the same applications as the sanitizer or disinfectant. For example, a veterinary pharmaceutical use of an ionene polymer containing triiodide includes the treatment of udder infections (Mastitis prevention) in dairy cattle. This use provides an example of benefits from both the ionene polymer and the biologically-active anion.

Mastitis is generally considered the most costly disease of dairy cows. Mastitis results in economic loss due to milk discard, early culling, drug costs, veterinary costs, and increased labor. Mastitis reduces the quantity and quality of milk and manufactured milk products. Mastitic infections reduce lactose, fat, solids-to-fat ratio, and casein. Economic incentives to control mastitis include public health, consumer acceptance and product shelf life. Although all these effects of mastitis result in considerable economic loss, decreased milk production is the single most important economic consideration. Udder hygiene is the most cost-effective means to control bovine mastitis. For many years, the dairy industry has emphasized proper attention to hygiene during milking, postmilking, and between milking.

Mastitis control is generally accomplished by a teat dip or an udder wash. Treatment formulations generally contain the following active ingredients: iodine, chlorhexidine, monomeric quaternary ammonium compounds, sodium hypochlorite, and dodecyl benzene sulfonic acid.

As discussed above, the present invention employs ionene polymers as the cationic backbone. Ionene polymers do possess anti-germicidal activity but generally need longer contact times to achieve the desired kill rates. One important aspect of ionene polymers, however, is their ability to form thin layers/films on anionic surfaces to maintain at least some bacteriostatic activity. When an ionene polymer according to the invention contains a triiodide anion, the iodine acts fast to disinfect the surface and as the free iodine is "used up", the ionene polymer remains to extend the anti-germicidal protection.

Another practical use not already mentioned for iodinated ionene polymers according to the invention (e.g. those with an $I_3^-$ anion), is hard surface sanitization/disinfection. Iodine based sanitizers described in this invention are non-odorous, non-irritating, non-corrosive, effective in hard water, effective at high pH, low foaming, and somewhat more stable in the presence of organic matter than are the chlorine based compounds. Iodophors in general have a non-rinse label claim for food contact surfaces and a broad spectrum of activity against bacteria and viruses, including tuberculosis. In most iodine based sanitizers or disinfectants, elemental iodine is complexed to nonionic surface-active agents such as nonyl phenol ethylene oxide condensates or to a carrier such as polyvinylpyrrolidone to form the "iodophors."

The ionene polymers of the invention can also complex with surface active agents yielding detergent-like properties. The ionene polymers of this invention having iodine directly bound to the cationic polymer give both surface active properties and fast acting sanitization properties qualifying them as detergent-sanitizers.

One use of such polymers is in the food industry. The use of iodine-based ionene polymers will stain soils yellow. This staining indicates the location of inadequate cleaning on equipment or surfaces.

Additional pharmaceutical uses of iodinated ionene polymers of the invention can also include, for example, topical antiseptics as a pre-surgery scrub or wound cleansing/disinfectant agent. Thus, they can be used to impregnate gauze in bandages to prevent opportunistic cutaneous infections. These ionene polymers can also be employed as textile disinfectants to disinfect hospital laundry sheets or other medical clothes or clothing, preferably at levels to prevent staining usually associated with iodine tinctures. Thus, the ionene polymer iodophors of this invention can be washed out using normal washing procedures.

In addition, the iodine-based ionene polymers of this invention can be used as algicides in recreational or industrial waters such as swimming pools and cooling tanks. With regard to this use, the teachings of the article "Effectiveness of Iodine for the Disinfection of Swimming Pool Water" Am. Journal of Public Health, V. 49(8) 1959, pp. 1060–1068, is incorporated herein by reference.

Due to their affinity for surfaces, ionene polymers containing biologically-active anions according to the invention can also be used in directed-delivery, timed-release, or sustained-release applications. The surface affinity of the cationic ionene polymer backbone allows the polymers to adhere to a surface. This has at least three distinct advantages.

First, the biologically-active anion can be delivered directly to a surface. For example, a herbicidal ionene polymer can bound directly to a plant surface exposing the herbicide directly to the plant.

Second, because the biologically-active anion is ionically bound to the cationic ionene polymer backbone, the binding of the ionene polymer to the surface "holds" the biologically-active anion in place. This advantageously allows more of the biologically-active anion to be available under conditions where the corresponding biologically-active compound, HA, may be lost or washed off due to its failure to bind strongly to the surface.

Third, over time the biologically-active anion will dissociate from the cationic ionene polymer and be replaced by other anionic moieties at the surface. This dissociation allows timed-release and/or sustained-release of the biologically-active anion to occur. Because the biologically-active anion distribution occurs all along the ionene polymer backbone, the folding of the polymer allows those anions nearer the surface to dissociate first and those within the folded polymer to dissociate at a later time. This releases the biologically-active anion over a prolonged time period, increasing its residence time on the surface and lengthening its desired effect.

The invention will be illustrated by the following examples, which, it will be understood, are not intended to be limiting, but merely illustrative.

EXAMPLE 1

Preparation of a Herbicidal Ionene Polymer

A one liter, three neck, round bottom flask was fitted with an agitator, condenser, thermometer and an addition funnel. The flask was then charged with 67.7g of an 85.7% solution of tetramethylethylene diamine (TMEDA) in water (0.5 mol TMEDA). To this solution was added 22.1 g (0.1 mol) of the herbicide 2,4-D. The solid 2,4-D dissolved in the aqueous amine solution and reacted with the TMEDA to form a partial amine salt. The reaction solution was then diluted with 100g of water, cooled with an ice bath and 86.3 g of a 37% hydrochloric acid solution (0.9 mol HCl) added incrementally to fully protonate the TMEDA while keeping the temperature below 40° C. Over a period of about 47 minutes, 92.5 g (1.0 mol) of epichlorohydrin was added, incrementally while maintaining the temperature between 50° C. and 60° C. Then additional TMEDA, 67.6 g of the 85.7% solution (0.5 mol), was added slowly over a period of about 46 minutes while maintaining the temperature between 50° and 60° C. Finally, the reaction solution was heated for about four hours while allowing the temperature to rise to 96° C. to effect polymerization. The resulting herbicidal ionene polymer had a weight average molecular weight of about 3500 as determined by aqueous gel permeation chromatography (GPC). The degree of substitution was about 5% 2,4-D and 95% chloride ion. The polymer was used as obtained without further work up. The concentration of the polymer in the resulting solution was about 60% by weight which corresponds to 5% by weight of 2,4-D in the solution.

EXAMPLE 2

Preparation of Disinfectant Ionene Polymer

Following a process substantially as described for Example 1, an ionene polymer was prepared in which a phenolate anion comprised a fraction of the anionic portion of the polymer. A 500 ml three necked flask, equipped with an agitator, condenser, thermometer, and addition funnel, was charged 153.42 g of water and 29.01 g (0.25 mol) of TMEDA. The solution was cooled with an ice bath and 4.5 g (0.05 mol) of phenol added to form a partial TMEDA—phenolate salt. Then 44.52 g of 37% hydrochloric acid was slowly added dropwise to fully protonate the TMEDA, while maintaining the temperature below 30° C. The pH was then adjusted to 4.04 with additional HCl. To this solution, 46.31 g (0.5 moles) of epichlorohydrin was added incrementally over a period of about forty five minutes maintaining the temperature between 50° C. and 60° C. The temperature of the solution was held between 50° C. and 60° C. for an additional period of about an hour, following which it was allowed to cool to about 40° C. An additional charge of TMEDA was made, 29.06 g (0.25 mol) over a period of 55 minutes maintaining the temperature between 55° C and 65° C. The temperature of the solution was then raised to between 80° C. and 90° C. for a period of about two and one half hours to effect polymerization. GPC analysis of the product indicated the molecular weight of the ionene polymer thus made to be about 3600. The degree of substitution of the anionic portion of the polymer was about 5% phenolate ion and 95% chloride. The concentration of the polymer in the resulting solution was about 46.8% by weight which corresponds to a 1.5% by weight of phenolate in the solution.

EXAMPLE 3

Preparation of an Ionene Plant Growth Regulator

Following substantially the same procedure described in Example 1, an ionene polymer was prepared in which 3-Indole butyric acid was the source of the biologically-active anions. A 500 ml three necked flask was equipped with an agitator, condenser, thermometer, and addition funnel and 158.82 g of water and 29.00 g (0.25 mol) of TMEDA was added to the flask. The solution was then cooled with an ice bath. To the amine solution was added 10.15 g (0.05 moles) of 3-indole butyric acid to form a partial amine salt of the TMEDA. Then 44.39 g of 37% hydrochloric acid was slowly added to fully protonate the TMEDA, while maintaining the temperature below 30° C. To this solution of the TMEDA amine salt was added 46.25 g (0.5 mol) of epichlorohydrin in increments over a period of about 108 minutes, while maintaining the temperature between 45° C. and 50° C. The temperature of the solution was slowly increased to 80° C. over a period of about 87 minutes, following which it was allowed to cool to about 60° C. An additional charge of 29 g (0.25 mol) of TMEDA was made over a period of 61 minutes while maintaining the temperature between 50° C. and 64° C. The temperature of the solution was then raised to 90° C. for a period of about two hours. GPC analysis of the product indicated the molecular weight of the ionene polymer thus made to be about 3600. The degree of substitution of the anionic portion of the polymer was about 5% of the plant growth regulator anion and 95% chloride. The concentration of the polymer in the solution was 45.7% by weight which corresponds to 3.5% by weight of the plant growth regulator in solution.

EXAMPLE 4

Preparation of an Aspirin-Containing Ionene Polymer

The procedure in Example 1 was followed to prepare an ionene polymer in which aspirin (acetyl salicylic acid) was the biologically-active anion. To a 1000 ml three necked flask, equipped with an agitator, condenser, thermometer, and addition funnel, 180.0 g of water, and 58.0 g (0.5 mol) of TMEDA was added. The solution was cooled with an ice bath 18.19 g (0.1 mol) of acetyl salicylic acid (aspirin). Then 56.95 g of 37% hydrochloric acid was slowly added to fully protonate the TMEDA, while maintaining the temperature below 40° C. To this solution of the TMEDA amine salt was added 92.5 g (1.0 mol) of epichlorohydrin in increments over a period of about 60 minutes while maintaining the temperature between 34° C. and 51° C. The solution was allowed to sit overnight during which time the temperature decreased to 25° C. An additional charge of TMEDA was made, 58.0 g (0.5 mol), over a period of 108 minutes while maintaining the temperature between 38° C. and 49° C. The temperature of the solution was then raised to 92° C. for a period of about two hours. The degree of substitution, D.S., of the anionic portion of the polymer was about 5% aspirin and about 95% chloride. The concentration of the polymer in the solution was 57.9% by weight which corresponds to 4.25% by weight of aspirin in solution.

EXAMPLE 5

Preparation of an Ionene Polymer Sun Screen Agent

The procedure of Example 1 was followed to prepare an ionene polymer in which p-amino benzoic acid was the source of the biologically-active anions. To a 500ml three necked flask, equipped with an agitator, condenser, thermometer, and addition funnel, 155.50 g of water and 29.01 g (0.25 mol) of TMEDA was added. The solution was cooled with an ice bath. P-aminobenzoic acid, 6.85 g (0.05 mol), to the amine solution was added. Then 44.40 g of 37% hydrochloric acid was slowly added to fully protonate the TMEDA, while maintaining the temperature below 30° C. To this solution of the TMEDA amine salt was added 46.30 g (0.5 mol) of epichlorohydrin in increments over a period of about 20 minutes while maintaining the temperature between 37° and 43° C. An additional charge of TMEDA was made, 29.01 g (0.25 mol) over a period of 17 minutes while maintaining the temperature between 42° and 49° C. The temperature of the solution was then raised to about 79° C. for a period of about 81 minutes. The degree of substitution of the anionic portion of the polymer was about 5% of the sun screen anion and 95% chloride. The concentration of polymer in the solution was 45.7% by weight which corresponds to 2.42% by weight of the sunscreen agent.

EXAMPLE 6

Preparation of a Preservative Ionene Polymer

The procedure of Example 1 was followed to prepare an ionene polymer in which where p-hydroxybenzoic acid was the source of the biologically-active anions. To a 500ml three necked flask, equipped with an agitator, condenser, thermometer, and addition funnel, 127.62 g of water, and 29.0 g (0.25 mol) of TMEDA was added. The solution was then cooled with an ice bath and p-hydroxybenzoic acid, 6.93 g (0.05 mol), was added. Then, 44.41 g of 37% hydrochloric acid was slowly added while maintaining the temperature below 30° C. To this solution of the potential TMEDA amine salt epichlorohydrin, 46.28 g (0.5 mol) was added in increments over a period of about 27 minutes while maintaining the temperature between 35° C. and 45° C. The solution was then heated, maintaining the temperature between 40° C. and 45° C. for about 44 minutes. An additional charge of 29.01 g of TMEDA was made over a period of 10 minutes while maintaining the temperature between 43° C. and 51° C. The temperature of the solution was then raised to about 80° C. and maintained between 80° and 102° C. for a period of about 94 minutes. The degree of substitution of the anionic portion of the polymer was about 5% of the preservative anion and 95% chloride. The concentration of the polymer in solution was 50.01% by weight which corresponds to 2.71% by weight of the preservative anion.

EXAMPLE 7

Preparation of Ureadiamine

To a one liter flask, equipped with an agitator, condenser, and thermometer, 120.1 g (2 mol) of urea and 406.7 g (4 mol) of dimethylaminopropylamine was added. The mixture was slowly heated to about 165° C. over a period of 100 minutes. Large quantities of ammonia were being liberated during this time. The reaction was maintained at 160°–165° C. for approximately eight and one-half hours; with continued liberation of ammonia. The product was a golden brown liquid and was used without further work up. The ureadiamine (UDA) used in subsequent examples was prepared according to this example.

EXAMPLE 8

Preparation of Herbicidal Ureadiamine Ionene Polymer

The procedure of Example 1 was followed to prepare a ureadiamine ionene polymer in which 2,4-D was the source of the biologically-active anions. To a 500 ml three necked flask, equipped with an agitator, condenser, thermometer, and addition funnel, 180.0 g of water, and 118.1 g of the product of Example 7 (0.5 mol of ureadiamine). The solution was cooled with an ice bath and 22.3 g (0.1 mol) of 2,4-D added. Then, 88.2 g of 37% hydrochloric acid was slowly added to fully protonate the TMEDA, while maintaining the temperature below 50° C. To this solution of the ureadiamine salt was added 92.5 g (1.0 mol) of epichlorohydrin in increments over a period of about 3 hours while maintaining the temperature below 50° C. An additional charge of 118.1 g (0.5 mol) of ureadiamine was made over a period of 95 minutes while maintaining the temperature between 41° C. and 53° C. The temperature of the solution was then raised to about 100° C. and maintained at reflux, about 106° C., for a period of about 6 hours. The degree of substitution of the anionic portion of the polymer was about 5% of the herbicide anion and 95% chloride. The concentration of the polymer in solution was 68.1% by weight which corresponds to 3.96% by weight of the herbicide anion.

EXAMPLE 9

Variation of the Degree of Substitution for Ionene Polymeric Herbicides

A series of ionene polymeric herbicides was prepared in which the degree of substitution of the herbicide 2,4-D was varied from about 12.5% to 37.5%. The ionene polymers were prepared using the procedure of Example 1.

To a one liter three neck round bottom flask, fitted with an agitator, condenser, thermometer and an addition funnel, of water, 180 g and tetramethylethylenediamine, TMEDA, 58.3 g (0.5 mol) were added as shown in Table 3. To this solution the various amounts of 2,4-D as listed in the Table 3 was added. Slowly with cooling by way of an ice bath, of 37% HCl was added to the flask in the amounts listed in Table 3. Epichlorohydrin (Epi), 92.5 g (1.0 mol), was added while maintaining the temperature below 60° C. Then, additional TMEDA, 58.3 g (0.5 mol), was slowly added over a period of about an hour while maintaining the temperature between 60° C. Finally the solutions were heated for about four hours while allowing the temperature to rise to about 100° C. The degree of substitution was about 12.5%, 25%, and 37.5% of the anion derived from 2,4-D. Concentrations of the ionene polymers in the resulting solutions were 66.7%, 64.98%, and 68.41% by weight, respectively. The concentration of the herbicide in each solution was 12.18%, 21.72%, and 29.39% by weight, respectively.

TABLE 3

| \multicolumn{7}{c}{Variation of the 2,4-D Degree of Substitution of Ionene Polymers Containing 2,4-D Weights of Materials Used} |
| --- | --- | --- | --- | --- | --- | --- |
| $H_2O$ | TMEDA | 2,4-D | | HCl | Epi | TMEDA |
| (grams) | (grams) | (moles) | (grams) | (grams) | (grams) | (grams) |
| 180 | 58.3 | 0.25 | 55.81 | 36.58 | 92.5 | 58.3 |
| 180 | 58.3 | 0.50 | 111.63 | 21.97 | 92.5 | 58.3 |
| 180 | 58.3 | 0.75 | 167.45 | 3.44 | 92.5 | 58.3 |

EXAMPLE 10

Preparation of an Ionene Polymer Tri-Iodide

The same procedure of Example 1 was used to make an ionene polymer in which about 10 percent of the anions were $I_3^-$. To a one liter three neck round bottom flask fitted with an agitator, condenser, thermometer and an addition funnel is charged 528.4 g of water and 115.03 g of ureadiamine (Example 7, 0.5 moles). To this solution is added 212.37 g (0.95 moles) of a 57% solution of hydroiodic acid. The solution was cooled to 28° C.; the pH was 3.32. The epichlorohydrin, 92.5 grams (1.0 mole), was added all at once; the temperature remained at 28° C. The temperature increased over the next five minutes to 35° C. at which time an ice bath was used to cool the solution. The temperature was maintained near 35° C. for the next three hours. Then the contents of the flask were heated to about 50° C. for twenty minutes. To this solution was added more ureadiamine, 115.30 grams, all at once. Iodine 25.22 g (0.1 mole) was then added. The solution was dark, red-black in color. The contents were then heated to about 70° C. for one hour, during which time the color of the solution turned to a light transparent yellow. More iodine (27.30 g) was added at this point, the color turned dark red-black. The solution was then heated at reflux for an additional hour. The color remained dark red-black. The concentration of the polymer in the resulting solution was 46.2% by weight which corresponds to 17.67% by weight of $I_3^-$.

The dark color indicates that much of the iodine ($I_3^-$) has remained in the $I_3^-$ form. This polymer was then tested for microbiological activity, the results are in Tables 8, 9, 10, and 11–13.

EXAMPLE 11

Preparation of a Tri-Iodide/Hypoiodite/Ionene/Polymer Disinfectant

A) To a one liter three neck round bottom flask fitted with an agitator, condenser, thermometer and an addition funnel is charged 503.0 g of water and 115.0 g of ureadiamine (Example 7, 0.5 moles). To this solution is added 213.8 g (0.95 moles) of a 57% solution of hydroiodic acid. The solution was cooled to 28° C.; the pH was 2.65. Then epichlorohydrin, 92.5 g (1.0 mole), was added all at once; the temperature remained at 28° C. The temperature increased over the next three minutes to 35° C. at which time an ice bath was used to cool the solution. The temperature was maintained near 35° C. for the next three hours. Then the contents of the flask water heated to about 45° C. for twenty minutes. To this solution was added more ureadiamine, 115.29 grams all at once. Iodine, 25.70 g (0.1 moles) was then added. This solution was dark red-black. The contents were then heated to about 102° C. for two hours, during which time the color of the solution turned to a light transparent yellow. The yellow color indicates that much of the iodine ($I_3^-$) had disappeared. It is believed that hypoiodite ion ($OI^-$) was formed from the $I_2$ (or $I_3^-$). This polymer was then tested for microbiological activity. The concentration of the polymer in the resulting solution was 46.7% by weight which corresponds to 1.5% by weight of hypoiodite ions.

B) To a one liter three neck round bottom flask fitted with an agitator, condenser, thermometer and an addition funnel is charged 503.0 g of water and 115.0 g of ureadiamine (Example 7, 0.5 moles). To this solution is added 213.8 g (0.95 moles) of a 57% solution of hydroiodic acid. The solution was cooled to 28° C.; the pH was 2.65. Then epichlorohydrin, 92.5 g (1.0 mole), was added all at once; the temperature remained at 28° C. The temperature increased over the next three minutes to 35° C. at which time an ice bath was used to cool the solution. The temperature was maintained near 35° C. for the next three hours. Then the contents of the flask water heated to about 45° C. for twenty minutes. To this solution was added more ureadiamine, 115.29 g all at once. Iodine, 25.70 g (0.1 moles) was then added. This solution was dark red-black. The contents were then heated to about 102° C. for two hours, during which time the color of the solution turned to a light transparent yellow. The yellow color indicates that much of the iodine ($I_3^-$) had disappeared. It is believed that hypoiodite ion was formed from the $I_2$ (or $I_3^-$). This polymer was then tested for microbiological activity. The concentration of the polymer in the resulting solution was 46.9% by weight which corresponds to 4.1% by weight of $I_3^-$.

EXAMPLES 12–29

Preparation of Additional Ionene Polymers With Organic Biologically-Active Anions The procedures set out in Examples 1 and 8 were followed to synthesize the polymers listed in the following Tables 4 and 5, respectively. Each table lists the moles of each reactant used and the degree of the substitution (D.S.) for each polymer. The concentration of the product polymers in solution was 50% by weight. The concentration of the biologically-active anion in solution is shown in the Tables as a percentage by weight of the solution.

TABLE 4

Substituted TMEDA Based Ionene Polymers

| | | Moles of Reactants | | | | | | |
|---|---|---|---|---|---|---|---|---|
| Ex | Active Compound | Activity | TMEDA | Active acid | HCl | Epi | TMEDA | D.S. | Conc. Active |
| 12 | fluorescein | fluorescence | 0.25 | 0.0250 | 0.475 | 0.5 | 0.25 | 5.00% | 3.21% |
| 13 | bromo-hydroxy-acetophenone | microbicide | 0.25 | 0.0250 | 0.475 | 0.5 | 0.25 | 5.00% | 2.13% |
| 14 | gallic acid | astringent | 0.25 | 0.0750 | 0.425 | 0.5 | 0.25 | 15.00% | 1.69% |
| 15 | citric acid | scale control | 0.25 | 0.0750 | 0.425 | 0.5 | 0.25 | 15.00% | 1.90% |
| 16 | gibberellic acid | plant growth regualtor | 0.25 | 0.0025 | 0.4498 | 0.5 | 0.25 | 0.50% | 0.003% |
| 17 | o-phenylphenol | microbicide sanitizer | 0.25 | 0.0050 | 0.475 | 0.5 | 0.25 | 5.00% | 1.69% |
| 18 | guanidine acetic acid | microbicide | 0.25 | 0.0400 | 0.460 | 0.5 | 0.25 | 8.00% | 1.18% |
| 19 | 3-indole propionic acid | plant growth regulator | 0.25 | 0.0400 | 0.460 | 0.5 | 0.25 | 8.00% | 1.87% |
| 20 | 1-amethoptherin | cancer treatment | 0.25 | 0.0001 | 0.500 | 0.5 | 0.25 | 0.02% | 2.00% |
| 21 | trans-beta hydromuconic acid | microbicide | 0.25 | 0.0625 | 0.438 | 0.5 | 0.25 | 12.50% | 3.45% |
| 22 | citronellic acid | pesticide | 0.25 | 0.0250 | 0.475 | 0.5 | 0.25 | 5.00% | 1.69% |
| 23 | abietic acid | sizing agent | 0.25 | 0.0001 | 0.500 | 0.5 | 0.25 | 0.02% | 0.012% |
| 24 | stearic acid | surfactant | 0.25 | 0.0250 | 0.475 | 0.5 | 0.25 | 5.00% | 2.76% |

TMEDA = tetramethyldiamine
Epi = epichlorohydrin

TABLE 5

Substituted Ureadiamine Ionene Polymers

| | | Moles of Reactants | | | | | | |
|---|---|---|---|---|---|---|---|---|
| Ex | Active Compound | Activity | UDA | Active acid | HCl | Epi | UDA | D.S. | Conc. Active |
| 25 | fluorescein | fluorescence | 0.25 | 0.025 | 0.475 | 0.5 | 0.25 | 5.00% | 2.19% |
| 26 | bromo-hydroxy-acetophenone | microbicide | 0.25 | 0.0750 | 0.425 | 0.5 | 0.25 | 5.00% | 1.45% |
| 27 | citronellic acid | plant growth regulator microbicide | 0.25 | 0.0025 | 0.425 | 0.5 | 0.25 | 0.50% | 0.023% |
| 28 | o-phenylphenol | microbicide sanitizer | 0.25 | 0.0750 | 0.425 | 0.5 | 0.25 | 15.00% | 1.15% |
| 29 | 3-indole butyric acid | plant growth regulator | 0.25 | 0.0400 | 0.460 | 0.5 | 0.25 | 8.00% | 1.36% |

UDA = ureadiamine, Example 7
Epi = epichlorohydrin

EXAMPLE 30

Herbicidal Activity of a Herbicidal Ionene Polymer

The herbicidal ionene polymer product from Example 1 was tested for its herbicidal activity. The reaction product was diluted to such an extent that the concentration of 2,4-D in the solution was reduced to 0.4%. The effectiveness of this preparation of the herbicidal ionene polymer was then compared with that of a commercial 2,4-D product "WEED-B-GONE"; available from Chevron Chemical Co., also at 0.4% active ingredient. In side by side comparisons, the herbicidal ionene polymer preparation was clearly a more effective herbicide than the commercial product.

The mechanism of the herbicidal activity appeared to be different in that the polymeric composition turned the leaves of broadleaf weeds brown and brittle within one to two days whereas the commercial product showed no such leaf burning activity. The herbicidal ionene polymer composition also killed the weeds faster than the commercial product. Other advantages were noted by those conducting the test. For example, during spraying, it was possible to identify those areas already sprayed with the polymeric composition because due to its greater visibility, possibly due to its attachment to the leaf surface as described above.

MICROBIOLOGICAL EXAMPLES

Materials and Methods

ANTI-BACTERIAL ACTIVITY

For short contact anti-bacterial efficacy, suspension screens were performed in deionized water with a mixed bacterial inoculum which consisted of an equal mixture of *Pseudomonas aeruginosa*, ATCC 15442, *Staphylococcus aureus*, ATCC 6538, and *Enterobacter aerogenes*, ATCC 13048. Each individual strain was maintained and grown at 37° C. in Tryptone Glucose Extract agar (TGEA). Short contact assays employed twenty-four hour cultures. On the day of the assay, bacterial growth was removed from the plates with a sterile cotton tip and resuspended in sterile saline. Each culture was standardized turbidimetrically (650 nm) to approximately $4.0 \times 10^7$ cfu/ml. After standardization equal portions were mixed and used within 2 hours.

Stock biocide solutions were made up as 0.1% product in sterile deionized water and adjusted to test concentrations in deionized water. Short contact screens (5–10 minutes) were performed in test tubes loaded with 10.0 ml of test concentration made up in deionized sterile water. Forty (40) microliters of the mixed suspension was added per tube. After specified contact times, the test tubes were shaken and 1.0 ml of the suspension was transferred to 9 ml of a "universal" biocide deactivator solution blank which contains 3.0 g Lecithin, 30 ml polysorbate 80, 5.0 g sodium thiosulfate, 1.0 g sodium bisulfite, 1.0 g sodium metabisulfite, 1.0 g peptone, 1.0 g monopotassium phosphate, 1.0 g dipotassium phosphate, 1 liter distilled water, final pH 7.0. From that point on, serial ten-fold dilutions were performed with the same deactivator solution blanks. Survivors were enumerated by standard pour plating techniques in TGEA and viable bacteria calculated as colony forming units per ml. Percent survivors were calculated by the following formula:

$$\frac{(CFU/\text{ml treatment} - CFU/\text{ml untreated control})}{CFU/\text{ml treatment}} \times 100$$

To determine the ability of ionene polymers of the invention to withstand a heavy organic load, the above procedure was employed with the exception that the molecules were made up in 5% bovine serum albumin (Sigma Chem Co. Fraction V) before challenge. For repeated challenge assays the procedures are as outlined above with the exception that several 40µl slugs of a mixed bacterial inoculum were introduced to the same biocide solution and enumerated after 5 minutes contact. Finally for individual bacterial efficacy screens, all Streptococcus species tested were grown and enumerated in 5% sheep blood agar all others were grown in TGEA (tryptone glucose extract agar) with the exception of *Candida albicans* which was grown and enumerated in non-acidified Potato Dextrose agar.

ANTI-FUNGAL ACTIVITY

Minimal fungistatic concentration (MFC) was determined by employing a mineral salts medium composed of ammonium nitrate 3.0 g, potassium phosphate 1.0 g, potassium chloride 0.25 g, magnesium sulfate 0.25 g, and Tween 80 product, 0.5 g, per liter deionized water (pH adjusted to 6.0). The day of the assay, a (36 hour old) *Aspergillus niger* culture was employed and a conidial (spore) suspension was obtained by removing spores with sterile pre-moisten cotton tip applicator. Spore suspensions were rigorously shaken to obtain a uniform suspension and turbidimetrically adjusted to an optical density of 0.2 at 650 nm. The biocide was made up as two-times the starting concentration desired and added at a 1:1 ratio to the first tube which contained two-times mineral salts medium. Subsequent two-fold dilutions were made in one-time mineral salts medium. After biocide dilutions each tube was inoculated with 40 µl of fungal spores and tubes incubate at 30° C. for 7 days. Control tubes did not have biocide. The minimal fungistatic concentration (MFC) was defined as the lowest concentration of biocide that exhibited no fungal growth.

ALGISTATIC ACTIVITY

Minimal algistatic concentration (MAC) was obtained with grown in Allen's medium composed of sodium nitrate 1.0 g, ammonium chloride 50 mg, calcium chloride 58 mg, magnesium sulfate 0.513 g, dipotassium phosphate 0.25 g, ferric chloride 3 mg per liter deionized water (pH adjusted to 7.0). The test were performed with a two week algal suspensions. The minimal algistatic concentration (MAC) has been defined as the lowest concentration of biocide that exhibited no algae growth.

The following ionene polymers and other polymers were used for comparison in various examples. Each of these polymers is available from Buckman Laboratories, Memphis, Tenn. Other comparative substances are identified in the particular example in which they were used.

Comparative Polymers

Busan® 77 product and WSCP™ product:
 a 60% by weight aqueous solution of poly[oxyethylene-(dimethyliminio)ethylene(dimethyliminio)ethylene-dichloride].

Bufloc® 1090 product and BL® 1090 product:

a 50% by weight aqueous solution of the ionene polymer formed by the reaction of 1,3-bis-dimethylaminopropylurea and 1,3-dichloro-2-isopropanol.

Busan® 1157 product and BL® 1157 product:

a 50% by weight aqueous solution of a dimethylamine epichlorohydrin crosslinked polymer.

PVP:

a 10% by weight solution of a polyvinylpyrrolidone polymer.

PVP-I (Betadine®, a product of the Purdue Fredrick Co., Norwalk, Conn.):

a 10% by weight solution of a polyvinylpyrrolidone polymer having a 1% by weight active iodine.

RESULTS

The microbiological activity of various ionene polymers according to the invention are shown in the following Tables 6–17. The concentrations shown are by weight.

The anti-bacterial efficacy of ionene polymers having organic biologically-active ions is shown in Table 6. The efficacy of ionene polymers according to the invention was tested using a minimum 5 minute contact time as recommended by the ASTM procedure to be an adequate contact time.

(1000 ppm) product in 5 minutes as with the urea diamine 2,4-D polymer.

Table 6 also demonstrates the potentiating effect which may be achieved incorporating the biologically-active anion into an ionene. The substituted phenol urea diamine ionene polymer of Example 28 demonstrates a >five log (>99.999%) reduction in bacterial growth at the 1000 ppm level. In comparison the unsubstituted unmodified urea diamine ionene polymer control, Bufloc® 1090, had only a two log (97.34%) reduction at the same concentration. This potentiating effect can advantageously provide a quicker kill of bacterial growth as well as a broader spectrum of biocidal use.

The phytohormone substituted ionene polymers on the other hand did not show a potentiating effect against this mixed bacterial inoculum. Nonetheless, the substitution did not affect the ionene polymer's own anti-bacterial activity and combined that activity with the anti-Legionella activity of the phytohormone. This added activity was in part the rational for incorporating these phytohormones as biologically-active anions. Recent publications have implicated certain phytohormones (i,.e., indole-3-propionic acid) of having activities against the respiratory pathogen *Legionella*

TABLE 6

Anti-Bacterial Efficacy, Organic Biologically-Active Ions
5 min contact time

| Example | 50 ppm | 100 ppm | 400 ppm | 1000 ppm | Biologically-active compound |
|---|---|---|---|---|---|
| 1 | 97.30 | 99.75 | 98.85 | 99.99 | 2,4-D |
| 28 | 97.30 | 97.55 | 99.99 | >99.999 | ortho phenyl phenol |
| 2 | 96.00 | 96.95 | 99.99 | >99.999 | phenol |
| 17 | nd | 98.91 | nd | 99.99 | ortho phenyl phenol |
| 19 | nd | 89.13 | nd | 99.98 | 3-indole butyric acid |
| 13 | nd | 69.56 | nd | 91.30 | bromohydroxy acetophenone |
| Bufloc ® 1090 | nd | 94.03 | nd | 99.34 | — |

Bioburden introduced $5.0 \times 10^6$ cfu/ml

Based on the results shown in Table 6, the phenol substituted urea diamine ionene polymer of Example 28 demonstrated the most effective short contact efficacy against the mixed bacterial inoculum (>five log, >99.9997, reduction in 5 minutes contact with 0.1% product). The substituted phenol urea diamine ionene polymer of Example 28 qualifies as surface sanitizers with a concentration of 400 ppm (ASTM recommends obtaining a three log, 99.9%, reduction within 5 minutes) product. As can be seen from Table 6, the other ionene polymers of this invention were also effective in obtaining a four log (99.99%) reduction with a 0.1%

*pneumophila* (Maldelbaum et al., 1991 Susceptibility of *Legionella pneumophila* Grown Extracellularly and in Human Monocytes to Indole-3-propionic Acid, "Antimicrobial, Agents and Chemotherapy 35:2526–2530) known to cause Legionnaire's Disease.

Among the most active inorganic anions tested were the triiodinated ionenes. Short contact efficacies were also obtained with the suspension screen described in the Material and Methods section above. The results are shown in Tables 7–9.

TABLE 7

Contact suspension screen against a mixed bacterial inoculum.

| | Percent reduction (ppm product) | | | | | | | |
|---|---|---|---|---|---|---|---|---|
| Example | 5 ppm[a] | 10 ppm[a] | 25 ppm[a] | 50 ppm[a] | 100 ppm[a] | 100 ppm[b] | 1000 ppm[b] | active |
| 11A | 99.65 | 99.84 | 99.77 | 99.83 | 99.91 | 96.34 | ≧99.999 | iodine |
| 11B | 98.8 | 97.31 | 98.13 | 97.10 | 97.10 | 99.13 | 99.998 | iodine |

TABLE 7-continued

Contact suspension screen against a mixed bacterial inoculum.

| Example | Percent reduction (ppm product) | | | | | | | active |
|---|---|---|---|---|---|---|---|---|
| | 5 ppm[a] | 10 ppm[a] | 25 ppm[a] | 50 ppm[a] | 100 ppm[a] | 100 ppm[b] | 1000 ppm[b] | |
| 10 | 76.31 | 94.47 | 99.63 | 99.99 | 99.99 | 70.43 | nd | iodine |
| Busan ®77 | nd | nd | 89.59 | 86.12 | 88.36 | nd | nd | — | nd = not determined.
[a] = 10 minute contact time, bioburden introduced $2.9 \times 10^6$ cfu/ml.
[b] = 5 minute contact time, bioburden introduced $4.9 \times 10^6$ cfu/ml Based on the results in Table 7, both iodinated ionenes showed greater percentage kill to a mixed bacterial population than the unsubstituted ionene. At 1000 ppm (product) concentration the iodinated ionenes had a greater than or equal to 4–5 log reduction in 5 minutes contact, qualifying them as good sanitizer molecules. As shown in Table 8 below, the contact time was also extended to 10 minutes and concentrations lower than 50 ppm tested. Approximately 1 log (90%) differences were observed at lower concentrations as compared to WSCP against a mixed bacterial inoculum.

TABLE 8

Suspension screen with 0.1% (1000 ppm) product against a mixed bacterial inoculum.

| | Percent reduction at varied contact times | | | |
|---|---|---|---|---|
| Example # | 30 sec. | 2 min. | 5 min. | 10 min. |
| 11A | 98.2 | 98.5 | 99.78 | 99.8 |
| 11B | 55.2 | 65.7 | 84.21 | 94.7 |
| 10 | 99.42 | 99.999 | ≧99.999 | ≧99.999 |
| CDQ[1] | >99.999 | ≧99.999 | ≧99.999 | ≧99.999 |
| PVP-I[2] | ≧99.999 | ≧99.999 | ≧99.999 | ≧99.999 |
| WSCP[3] | 65.0 | 55.9 | 77.7 | 85.0 |
| BL ®-1157[3] | 58.1 | 87.8 | 89.7 | 87.3 |
| BL ® 1090[3] | 99.96 | 99.98 | 99.99 | 99.99 |

Bioburden introduced: $1.0 \times 10^6$ cfu/ml.
[1]Nonpolymeric quaternary compound (control), Oxydiethlylenebis(alky dimethyl ammonium chloride), 36% active, available from Buckman Laboratory, Memphis, Tenn..
[2]Betadine ® product, (control) Purdue Frederick Company, Norwalk, Connecticut, 10% solution polyvinyl pyrrolidine iodine.
[3]Unsubstituted ionene tested at 0.5% (5000 ppm) product A third suspension screen was performed; this time at 1000 ppm with shorter contact times. The results are shown in Table 9 below. Based on the results obtained, the biologically-active ionene polymer of Example 10 had greater than or equal to 5 log (99,999%) reduction with in two minutes contact at 1000 ppm. In comparison, the most effective unsubstituted ionene tested produced only a 4 log (99.99%) reduction in 10 minutes with a higher concentration of 5000 ppm.

In order to determine the ability of these molecules to withstand an organic burden, several efficacy experiments were conducted in the presence of organic burden, such as the addition of bovine serum albumin to the system. This ability of the biocide to withstand organic load is necessary if these were utilized as multipurpose sanitizers (home or industrial). Table 9 shows that tri-iodide ionene polymers according to the invention, exemplified by the polymer of Example 11A, obtained at least a 2 log (99%) reduction in the presence of 5% bovine serum albumin.

TABLE 9

Effect of organic load on iodinated ionenes.

| Compound Example 11A | 0.5% (w/o BSA) | 0.5% (5% BSA) |
|---|---|---|
| 30 sec. | 99.999 | 98.86 |
| 2 min. | ≧99.999 | 99.61 |
| 5 min. | ≧99.999 | 99.88 |
| 10 min. | ≧99.999 | 99.95 |

BSA = Bovine serum albumin, fraction 5 (Sigma Chem. Co.).

An assay was performed in which multiple bacterial challenges were spiked into the same biocide solution. The results in Table 10 showed consistent biocidal activity after 5 bacterial slugs. At least a 5 log (99,999%) reduction was achieved after 5 minutes contact, while, as expected, the control numbers increased per spike.

TABLE 10

Repeated bacterial challenges to a 0.5% solution in deionized water of the iodinated ionenes of Examples 11A and 10.

| | Percent Reduction (5 minutes contact) | | | |
|---|---|---|---|---|
| Challenge | Example 11A | Saline Control | Example 10 | Saline Control |
| #1 | 99.999 | $1.32 \times 10^6$ cfu/ml | ≦99.999 | $1.0 \times 10^6$ cfu/ml |
| #2 | 99.999 | $4.30 \times 10^6$ cfu/ml | ≧99.999 | $5.0 \times 10^6$ cfu/ml |
| #3 | 99.999 | $5.20 \times 10^6$ cfu/ml | ≦99.999 | $7.1 \times 10^6$ cfu/ml |
| #4 | 99.999 | $1.03 \times 10^7$ cfu/ml | ≧99.999 | $1.0 \times 10^7$ cfu/ml |
| #5 | 99.999 | $1.29 \times 10^7$ cfu/ml | ≦99.999 | $1.8 \times 10^7$ cfu/ml |

Challenges were performed every 6 minutes.

The ability to withstand an organic load is critically important when sanitizing dirty surfaces such as the ones encountered in the dairy industry or food industry. Having established that tri-iodide ionene polymers according to the invention can withstand a heavy organic load without losing all its activity, the efficacies of these polymers to particular pathogens commonly incriminated as causative agents of mastitis in dairy cattle was then determined. The results are shown in Table 11.

TABLE 11

| | Example 11A (0.1% solution) Percent Reduction | | | |
|---|---|---|---|---|
| Organism | 30 sec. | 2 min. | 5 min. | 10 min. |
| S. aureus | 99.65 | 99.75 | 99.87 | 99.96 |
| E. coli | ≥99.999 | ≥99.999 | ≥99.999 | ≥99.999 |
| E. aerogenes | 84.0 | 94.0 | 99.36 | 99.92 |
| S. agalactiae[1] | 99.0 | 99.98 | ≥99.998 | ≥99.999 |
| S. uberis[1] | 69.7 | 88.3 | 98.60 | 99.97 |
| S. dysgalactiae | 10.2 | 53.0 | 40.8 | 67.3 |
| P. aeruginosa[1] | ≥99.999 | ≥99.999 | ≥99.999 | ≥99.999 |
| C. albicans[1] | 37.5 | 65.8 | 70.8 | 85.3 |

[1]concentration made up as 0.5% product for this particular strains.

Based on the data in Table 11, it can be observed that the iodinated ionene polymer of Example 11A was very effective against (0.1%) *Escherichia coli* and *Pseudomonas aeruginosa* (0.5%). A 3 log (99.9%) or greater reduction was achieved against common mastitis pathogens with the exception of *Candida albicans* (0.5%).

The ionene polymer of Example 11B also, as shown in Table 12 below, demonstrated significant efficacy against these selected pathogens. Comparing the results in Tables 11 and 12, the ionene polymer of Example 11B, with a greater degree of substitution, showed greater efficacy than the ionene polymer of Example 11A.

TABLE 12

| | Example 11B (0.1% solution) Percent Reduction | | | |
|---|---|---|---|---|
| Organism | 30 sec. | 2 min. | 5 min. | 10 min. |
| A. pyogenes[2] | 90.9 | 99.7 | 99.97 | 99.99 |
| S. aureus | 99.71 | ≥99.999 | ≥99.999 | ≥99.999 |
| E. coli | ≥99.999 | ≥99.999 | ≥99.999 | ≥99.999 |
| E. aerogenes | ≥99.999 | ≥99.999 | ≥99.999 | ≥99.999 |
| S. agalactiae | 99.86 | 99.98 | ≥99.999 | ≥99.999 |
| S. uberis | 99.999 | ≥99.999 | ≥99.999 | ≥99.999 |
| S. dysgalactiae | 59.1 | 99.2 | 99.99 | 99.998 |
| P. aeruginosa | ≥99.999 | ≥99.999 | ≥99.999 | ≥99.999 |
| C. albicans | ≥99.999 | ≥99.999 | ≥99.999 | ≥99.999 |

[2]Concentration made up as 0.5% product for this particular organism.

Table 13 depicts the efficacy of yet another ionene according to the invention, the iodinated ionene polymer of Example 10. In this case that ionene appears to be slightly more efficacious than the ionene polymer of Example 11B. The degree of substitution appears to have a direct relationship to the degree of activity observed. The ionene polymer of Example 11A was the lightest in color, followed by that of Example 11B and then the darkest was the ionene polymer of Example 10. The amber color correlates to the degree of substitution of iodine.

TABLE 13

| | Example 10 (0.1% solution) Percent Reduction | | | |
|---|---|---|---|---|
| Organism | 30 sec. | 2 min. | 5 min. | 10 min. |
| S. uberis | ≥99.999 | ≥99.999 | ≥99.999 | ≥99.999 |

TABLE 13-continued

| | Example 10 (0.1% solution) Percent Reduction | | | |
|---|---|---|---|---|
| Organism | 30 sec. | 2 min. | 5 min. | 10 min. |
| S. dysgalactiae | 99.998 | 99.998 | 99.998 | 99.998 |
| E. aerogenes | 99.98 | 99.99 | ≥99.999 | ≥99.999 |

The fungistatic efficacy of the iodinated ionene polymer of Examples 10 and 11 was tested by determining the minimal fungistatic concentration (MFC) against *Aspergillus niger*. The results are shown, together with various controls, in Table 14.

TABLE 14

Minimal fungistatic concentration (MFC) of selected substituted triiodinated ionenes and other molecules against *Aspergillus niger*

| Example | MFC | Biologically-Active Anion |
|---|---|---|
| 11A | 20,000 ppm | triiodide |
| 11B | 20,000 ppm | triiodide |
| 10 | 2500 ppm | triiodide |
| BL ®-1090 | 5000 ppm | — |
| PVP-I | 2500 ppm | — |
| PVP | >20,000 ppm | — |

The algistatic efficacy of the iodinated ionene polymers of Examples 10 and 11 was tested by determining the minimum inhibitory concentration (MIC) against three species of algae. The results are shown in Table 15.

TABLE 15

Algistatic Efficacy of Selected Substituted Ionene Compounds

| | Minimum Inhibitory Concentration (ppm) | | |
|---|---|---|---|
| Example | C. pyrenoidosa | C. hypnosporum | P. inumdatum |
| 11A | nd | 3 | 3 |
| 11B | 5 | 2 | 2 |
| WSCP ™ | 2 | 2 | 8 |
| Busan ®1157 | 4 | 4 | nd | nd = not determined

From this disclosure, it will be apparent to those skilled in the art that various modifications and variations of the present invention can be made without departing from the spirit or scope of the invention. Thus, the present invention intentionally covers such modifications and variations of this invention coming within the scope of the appended claims and their equivalents.

The claimed invention is:

1. A water-soluble ionene polymer of formula I:

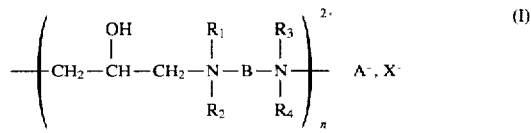

wherein n is an integer from 4 to 400 corresponding to the degree of polymerization of the polymer;

$R_1$, $R_2$, $R_3$ and $R_4$ represent the same or different substituent selected from the group consisting of hydrogen, a $C_1$ to $C_{16}$ alkyl group, a $C_1$ to $C_{16}$ alkyl group substituted with one or more hydroxyl groups, a benzyl group, and a benzyl group substituted with one or more $C_1$ to $C_{16}$ alkyl groups;

B represents a divalent $C_2$ to $C_{16}$ aliphatic hydrocarbon radical which can be substituted by hydroxyl, a divalent $C_5$ to $C_9$ cyclic hydrocarbon radical, a di-($C_2$ to $C_6$)-alkylene ether, a phenylene or alkyl-substituted phenylene radical, or the divalent group $R_1R_2NBNR_3R_4$ of formula I represents a divalent radical of the structure:

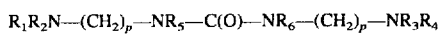

where p is an integer from 2 to 6, $R_1$, $R_2$, $R_3$ and $R_4$ are the same as defined above, and $R_5$ and $R_6$ are the same or different and are selected from the group consisting of hydrogen and a $C_1$ to $C_{16}$ alkyl group, or the divalent radical $R_1R_2NBNR_3R_4$ forms a heterocyclic group selected from 1,2-pyrazolidinyl, 1,3-imidazolindiyl, 1,4-piperazindiyl, aminopyrrolidinyl, or aminopiperidiyl wherein the heterocyclic group may be substituted with one or more groups selected from a $C_1$ to $C_6$ alkyl group, a hydroxyl group, a halide, or a phenyl group;

$A^-$ is an anion derived from a biologically-active compound having at least one acid functionality with the proviso that said anion is not a halide anion;

$X^-$ is an anion derived from a mineral or organic acid; and the degree of substitution of the polymer is from about 0.005 to 0.5.

2. An ionene polymer according to claim 1, wherein the anion $A^-$ is derived from a herbicide.

3. An ionene polymer according to claim 2, wherein the herbicide is 2,4-dichlorophenoxyacetic acid.

4. An ionene polymer according to claim 1, wherein the anion $A^-$ is derived from a disinfectant and the anion $X^-$ is selected from the group consisting of halide ions.

5. An ionene polymer according to claim 4, wherein the disinfectant is selected from the group consisting of phenol and phenol derivatives.

6. An ionene polymer according to claim 1, wherein the anion $A^-$ is derived from a pharmaceutical compound and the anion $X^-$ is selected from the group consisting of halide ions.

7. An ionene polymer of claim 1, wherein n is from 5–50;

$R_1$, $R_2$, $R_3$ and $R_4$ are each methyl, ethyl, or benzyl;

B is methylene, ethylene, propylene, 2-hydroxypropylene, butylene, isobutylene, diethylene ether, or phenylene; and $X^-$ is a halide.

8. An ionene polymer of claim 7, wherein $R_1$, $R_2$, $R_3$ and $R_4$ are each methyl, B is ethylene, and $X^-$ is chloride.

9. An ionene polymer of claim 1, wherein the group $R_1R_2NBNR_3R_4$ is a radical of the structure:

10. An ionene polymer of claim 9, wherein n is from 5–50;

$R_1$, $R_2$, $R_3$ and $R_4$ are each methyl, ethyl or benzyl;

$R_5$ and $R_6$ are each methyl or ethyl;

p is 2 or 3; and $X^-$ is a halide.

11. An ionene polymer of claim 10, wherein $R_1$, $R_2$, $R_3$, $R_4$, $R_5$ and $R_6$ are methyl, p is 3, and $X^-$ is a halide.

12. The ionene polymer of claim 1 wherein the anion $A^-$ is $I_3^-$.

13. A method for the preparation of an ionene polymer of formula I according to claim 1, the method comprising the steps of:

reacting a protonated diamine of formula IV

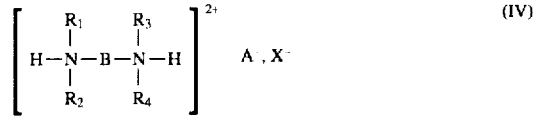

with an epihalohydrin under conditions sufficient to form an intermediate of formula VI

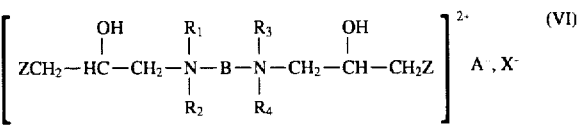

and polymerizing said intermediate with a diamine of formula III

under conditions sufficient to form said polymer.

14. A method of claim 13, further comprising, before said reaction step, the steps of neutralizing a diamine of formula III with up to one equivalent of a biologically-active acid, HA, per amine group; and adding sufficient acid, HX, so that the total amount of acid used is approximately equivalent to the amine groups present, thereby forming the protonated diamine of formula IV.

15. A method according to claim 13, wherein the epihalohydrin is epichlorohydrin.

16. A method of claim 13, wherein the anion $A^-$ is $I_3^-$.

17. A method of claim 13, wherein the anion $A^-$ is a phenolate anion.

18. A water-soluble ionene polymer of formula II:

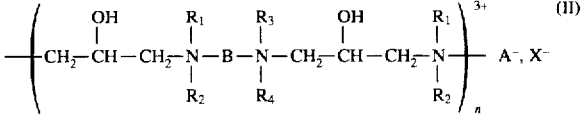

wherein n is an integer from 4 to 400 corresponding to the degree of polymerization of the polymer;

$R_1$, $R_2$, $R_3$ and $R_4$ represent the same or different substituent selected from the group consisting of hydrogen, a $C_1$ to $C_{16}$ alkyl group, a $C_1$ to $C_{16}$ alkyl group substituted with one or more hydroxyl groups, a benzyl group and a benzyl group substituted with one or more $C_1$ to $C_{16}$ alkyl groups;

B represents a divalent $C_2$ to $C_{16}$ aliphatic hydrocarbon radical which can be substituted by hydroxyl, a divalent $C_5$ to $C_9$ cyclic hydrocarbon radical, a di-($C^2$ to $C^6$)-alkylene ether, a phenylene or alkyl-substituted phenylene radical or the divalent group $R_1R_2NBNR_3R_4$ of formula II represents a divalent radical of the structure:

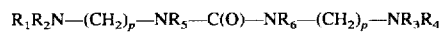

33 where p is an integer from 2 to 6, $R_1$, $R_2$, $R_3$, and $R_4$ are the same as defined above, and $R_5$ and $R_6$ are the same or different and are selected from the group consisting of hydrogen and a $C_1$ to $C_{16}$ alkyl group, or the divalent radical $R_1R_2NBNR_3R_4$ forms a heterocyclic group selected from 1,2-pyrazolidinyl, 1,3-imidazolindiyl, 1,4-piperazindiyl, aminopyrrolidinyl, or aminopiperidiyl wherein the heterocyclic group may be substituted with one or more groups selected from a $C_1$ to $C_6$ alkyl group, a hydroxyl group, a halide, or a phenyl group;

$A^-$ is an anion derived from a biologically-active compound having at least one acid functionality with the proviso that said anion is not a halide anion;

$X^-$ is an anion derived from a mineral or organic acid; and the degree of substitution of the polymer is from about 0.005 to 0.333.

19. An ionene polymer according to claim 18, wherein the anion $A^-$ is derived from a herbicide.

20. An ionene polymer according to claim 19, wherein the herbicide is 2,4-dichlorophenoxyacetic acid.

21. An ionene polymer according to claim 18, wherein the anion $A^-$ is derived from a disinfectant and the anion $X^-$ is selected from the group consisting of halide ions.

22. An ionene polymer according to claim 21, wherein the disinfectant is selected from the group consisting of phenol and phenol derivatives.

23. An ionene polymer according to claim 18, wherein the anion $A^-$ is $I_3^-$.

24. An ionene polymer of claim 18, wherein, n is from 5–50;

$R_1$, $R_2$, $R_3$ and $R_4$ are each methyl, ethyl, or benzyl;

B is methylene, ethylene, propylene, 2-hydroxypropylene, butylene, isobutylene, diethylene ether, or phenylene;

$X^-$ is a halide.

25. An ionene polymer of claim 24, wherein, $R_1$, $R_2$, $R_3$ and $R_4$ are each methyl, B is ethylene, and $X^-$ is chloride.

26. An ionene polymer of claim 18, wherein the group $R_1R_2NBNR_3R_4$ is a radical of the structure:

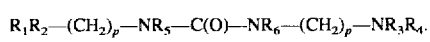

27. An ionene polymer of claim 26, wherein n is from 5–50;

$R_1$, $R_2$, $R_3$ and $R_4$ are each methyl, ethyl or benzyl;

$R_5$ and $R_6$ are each hydrogen, methyl or ethyl;

p is 2 or 3; and $X^-$ is a halide.

28. An ionene polymer of claim 26, wherein $R_1$, $R_2$, $R_3$ and $R_4$ are methyl, $R_5$ and $R_6$ are hydrogen, p is 3, and $X^-$ is a halide.

29. A method for the preparation of an ionene polymer of formula II according to claim 18, the method comprising the steps of:

34 reacting a protonated diamine of formula IV

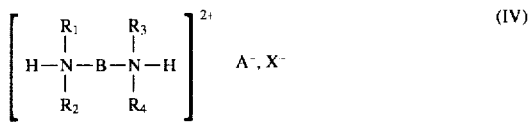

with an epihalohydrin under conditions sufficient to form an intermediate of formula VI

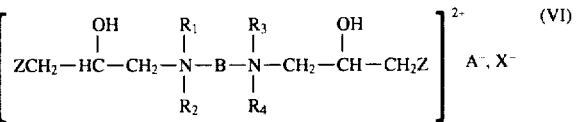

and polymerizing said intermediate with a secondary amine of formula VII

under conditions sufficient to form said polymer.

30. A method of claim 29, further comprising, before said reaction step, the steps of neutralizing a diamine with up to one equivalent of a biologically-active acid, HA, per amine group; and adding sufficient acid, HX, so that the total amount of acid used is approximately equivalent to the amine groups present, thereby forming the protonated diamine of formula IV.

31. A method according to claim 29, wherein the epihalohydrin is epichlorohydrin.

32. A method according to claim 30, wherein the biologically-active acid is the herbicide 2,4-dichlorophenoxyacetic acid.

33. A method according to claim 30, wherein the anion $A_-$ is a phenolate anion.

34. A method according to claim 29, wherein the anion $A^-$ is $I_3^-$.

35. A method for the preparation of an ionene polymer having a biologically-active anion comprising the steps of a) reacting a protonated diamine having at least one anion derived from a biologically-active compound, with the proviso that said anion is not a halide anion with an epihalohydrin, and b) polymerizing the product of step a) with a secondary amine or a diamine.

36. A compound of formula VI:

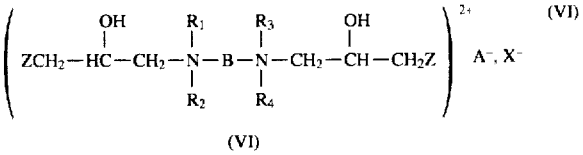

(VI)

wherein $R_1$, $R_2$, $R_3$ and $R_4$ represent the same or different substituent selected from the group consisting of hydrogen, a $C_1$ to $C_{16}$ alkyl group, a $C_1$ to $C_{16}$ alkyl group substituted with one or more hydroxyl groups, a benzyl group and a benzyl group substituted with one or more $C_1$ to $C_{16}$ alkyl groups;

B represents a divalent $C_2$ to $C_{16}$ aliphatic hydrocarbon radical which can be substituted by hydroxyl, a divalent $C_5$ to $C_9$ cyclic hydrocarbon radical, a di-($C_2$ to $C_6$)-alkylene ether, a phenylene or alkyl-substituted phenylene radical, or the divalent group $R_1R_2NBNR_3R_4$ in formula VI represents a divalent radical of the structure:

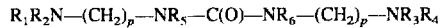
$$R_1R_2N-(CH_2)_p-NR_5-C(O)-NR_6-(CH_2)_p-NR_3R_4$$

where p is an integer from 2 to 6 and $R_5$ and $R_6$ are the same or different and selected from the group consisting of hydrogen and a $C_1$ to $C_{16}$ alkyl group, or the divalent radical $R_1R_2NBNR_3R_4$ forms a heterocyclic group selected from 1,2-pyrazolidinyl, 1,3-imidazolindiyl, 1,4-piperazindiyl, aminopyrrolidinyl, or aminopiperidiyl wherein the heterocyclic group may be substituted with one or more groups selected from a $C_1$ to $C_6$ alkyl group, a hydroxyl group, a halide, or a phenyl group;

$A^-$ is an anion derived from a biologically-active compound having at least one acid functionality with the proviso that said anion is not a halide anion; and $X^-$ is an anion derived from a mineral acid.

37. A compound of claim 36, wherein n is from 5–50;

$R_1$, $R_2$, $R_3$, $R_4$ are each methyl, ethyl, or benzyl;

B is methylene, ethylene, propylene, 2-hydroxypropylene, butylene, isobutylene, diethylene ether, or phenylene; and $X^-$ is a halide.

38. A compound of claim 37, wherein;

$R_1$, $R_2$, $R^3$, $R_4$ are each methyl,

B is ethylene, and $X^-$ is chloride.

39. A compound of claim 36, wherein the group $R_1R_2NBNR_3R_4$ is a radical of the structure:

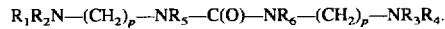
$$R_1R_2N-(CH_2)_p-NR_5-C(O)-NR_6-(CH_2)_p-NR_3R_4.$$

40. A compound of claim 39, wherein $R_1$, $R_2$, $R_3$ and $R_4$ are each methyl, ethyl or benzyl;

$R_5$ and $R_6$ are each hydrogen, methyl or ethyl;

p is 2 or 3; and $X^-$ is a halide.

41. A compound of claim 40, wherein $R_1$, $R_2$, $R_3$ and $R_4$ are methyl, $R_5$ and $R_6$ are hydrogen, p is 3, and $X^-$ is a halide.

42. A method according to claim 14, wherein the biologically-active acid is the herbicide 2,4-dichlorophenoxyacetic acid.

43. A fertilizer comprising a polymer of claim 1 or 18.

44. A pesticide comprising a polymer of claim 1 or 18.

45. A therapeutic agent comprising a polymer of claim 1.

46. A dispersant comprising a polymer of claim 1 or 18.

47. A microbicide comprising a polymer of claim 1 or 18.

48. A preservative comprising a polymer of claim 1 or 18.

49. A disinfectant comprising a polymer of claim 1 or 18.

50. A plant growth regulator comprising a polymer of claim 1 or 18.

51. A sizing agent comprising a polymer of claim 1 or 18.

52. A surfactant comprising a polymer of claim 1 or 18.

53. A herbicide comprising a polymer of claim 1 or 18.

54. A sanitizer comprising a polymer of claim 1 or 18.

55. A scale control agent comprising a polymer of claim 1 or 18.

56. A fluorescent agent comprising a polymer of claim 1 or 18.

57. A termicide comprising a polymer of claim 1 or 18.

58. A method for fertilizing comprising applying to foliage the fertilizer of claim 43.

59. A method to destroy pests comprising applying to the pests or to the locus of the pests the fertilizer of claim 44.

60. A method for promoting the formation and stabilization of a dispersion of at least one substance in another substance comprising adding the dispersant of claim 46 to the dispersion.

61. A method to destroy microorganisms comprising applying to the microorganisms or to the locus of the microorganisms the microbicide of claim 47.

62. A method to preserve a substance comprising applying or adding to the substance the preservative of claim 48.

63. A method for disinfecting a substance comprising applying to the substance the disinfectant of claim 49.

64. A method to regulate plant growth comprising applying to the plant or to the locus of the plant the plant growth regulator of claim 50.

65. A method to destroy or inhibit plant growth comprising applying to a plant or to the locus of the plant the herbicide of claim 53.

66. A method of sanitizing a substance comprising cleaning or sterilizing the substance with the sanitizer of claim 54.

67. A method to destroy termites comprising applying to the termites or to the locus of the termites the termiticide of claim 57.

68. A method to treat udder infections in dairy cattle comprising administering a pharmaceutically effective amount of a formulation comprising the polymer of claim 1 or 18.

69. An algicide comprising a polymer of claim 1 or 18.

70. A method for disinfecting water comprising applying or adding to said water the algicide of claim 69.

71. A topical antiseptic comprising the polymer of claim 1 or 18.

* * * * *

UNITED STATES PATENT AND TRADEMARK OFFICE
CERTIFICATE OF CORRECTION

PATENT NO. : 5,575,993

DATED : November 19, 1996

INVENTOR(S) : James A. Ward et al.

It is certified that error appears in the above-indentified patent and that said Letters Patent is hereby corrected as shown below:

In claim 33, column 34, line 36, "A." should read --A⁻--.

Signed and Sealed this

Twenty-seventh Day of May, 1997

Attest:

BRUCE LEHMAN

Attesting Officer

Commissioner of Patents and Trademarks

UNITED STATES PATENT AND TRADEMARK OFFICE
CERTIFICATE OF CORRECTION

PATENT NO.:   5,575,993
DATED     :   November 19, 1996
INVENTOR(S):  James A. WARD et al.

It is certified that error appears in the above-identified patent and that said Letters Patent is hereby corrected as shown below:

In column 14,   line 27, "anti-germicidal" should read -- germicidal --;

line 35, "anti-germicidal" should read -- germicidal --.

Signed and Sealed this

Sixteenth Day of September, 1997

*Attest:*

BRUCE LEHMAN

*Attesting Officer*   *Commissioner of Patents and Trademarks*